United States Patent
Fridman et al.

(10) Patent No.: US 9,585,390 B2
(45) Date of Patent: Mar. 7, 2017

(54) MATERIALS FOR DISINFECTION PRODUCED BY NON-THERMAL PLASMA

(75) Inventors: Gregory Fridman, Philadelphia, PA (US); Sin Park, Philadelphia, PA (US); Natalie Shainsky, Philadelphia, PA (US); Danil V. Dobrynin, Philadelphia, PA (US); Alexander Rabinovich, Cherry Hil, NJ (US); Gennady Friedman, Richboro, PA (US); Alexander Fridman, Philadelphia, PA (US); Moogega Cooper, Pasadena, CA (US); Ari D. Brooks, Cherry Hill, NJ (US); Suresh G. Joshi, Secane, PA (US); Alexander E. Poor, Philadelphia, PA (US); Utku K. Ercan, Philadelphia, PA (US); Mark Ingerman, Wynnewood, PA (US)

(73) Assignee: Drexel University, Philadelphia, PA (US)

( * ) Notice: Subject to any disclaimer, the term of this patent is extended or adjusted under 35 U.S.C. 154(b) by 522 days.

(21) Appl. No.: 13/813,750

(22) PCT Filed: Aug. 3, 2011

(86) PCT No.: PCT/US2011/046382
§ 371 (c)(1),
(2), (4) Date: Sep. 16, 2014

(87) PCT Pub. No.: WO2012/018891
PCT Pub. Date: Feb. 9, 2012

(65) Prior Publication Data
US 2015/0038584 A1    Feb. 5, 2015

Related U.S. Application Data

(60) Provisional application No. 61/370,392, filed on Aug. 3, 2010, provisional application No. 61/370,409, filed on Aug. 3, 2010.

(51) Int. Cl.
*A01N 37/30* (2006.01)
*A01N 37/46* (2006.01)
(Continued)

(52) U.S. Cl.
CPC .............. *A01N 37/30* (2013.01); *A01N 37/46* (2013.01); *A01N 61/00* (2013.01); *A61L 2/16* (2013.01)

(58) Field of Classification Search
CPC ........ A01N 37/30; A01N 37/46; A01N 61/00; A01N 25/02; A01N 25/34; A61L 2/16
See application file for complete search history.

(56) References Cited

U.S. PATENT DOCUMENTS

| 5,753,196 A | 5/1998 | Martens et al. |
| 6,706,243 B1 | 3/2004 | Sias et al. |

(Continued)

FOREIGN PATENT DOCUMENTS

| EP | 2160081 A1 | 3/2010 |
| WO | WO 2006/116252 A2 | 11/2006 |

(Continued)

OTHER PUBLICATIONS

Jean-Louis Brisset, et al, "Chemical Reactivity of Discharges and Temporal Post-Discharges in Plasma Treatment of Aqueous Media: Examples of Gliding Discharge Treated Solutions", Industrial & Engineering Chemistry Research, vol. 47(16), Aug. 1, 2008, 5761-5781.

(Continued)

*Primary Examiner* — Regina M Yoo
(74) *Attorney, Agent, or Firm* — Baker & Hostetler LLP

(57) ABSTRACT

Aspects of the present subject matter are directed to a method comprising contacting an fluid, optionally containing an added organic material, with a non-thermal plasma to form a disinfection composition, wherein the disinfection (Continued)

composition is a liquid, and contacting a surface with the disinfection composition, wherein the surface is at least partially disinfected upon contact with the disinfection composition. Additional aspects of the present subject matter are directed to a method comprising forming a disinfection composition by contacting an organic material with a non-thermal plasma, wherein the disinfection composition is a liquid. A further aspect of the present subject matter is directed to a disinfection composition comprising an organic material contacted by a non-thermal plasma, wherein the disinfection composition is a liquid.

17 Claims, 34 Drawing Sheets

(51) Int. Cl.
*A01N 61/00* (2006.01)
*A61L 2/16* (2006.01)

(56) References Cited

U.S. PATENT DOCUMENTS

| | | | |
|---|---|---|---|
| 8,048,930 | B2 | 11/2011 | Bobbert |
| 2003/0039673 | A1 | 2/2003 | Shanbrom |
| 2003/0143110 | A1* | 7/2003 | Kritzler .................... A61L 2/22 422/29 |
| 2006/0127271 | A1 | 6/2006 | Ruan et al. |
| 2006/0175266 | A1 | 8/2006 | Rima et al. |
| 2007/0104610 | A1 | 5/2007 | Houston et al. |
| 2007/0292941 | A1 | 12/2007 | Handique et al. |
| 2008/0099406 | A1 | 5/2008 | Ruan et al. |
| 2008/0247904 | A1 | 10/2008 | Paskalov |
| 2009/0098062 | A1 | 4/2009 | Bobbert |
| 2010/0021340 | A1 | 1/2010 | Buske et al. |
| 2010/0030132 | A1 | 2/2010 | Niezgoda et al. |
| 2010/0055086 | A1 | 3/2010 | Raad |
| 2010/0168499 | A1 | 7/2010 | Gutsol et al. |

FOREIGN PATENT DOCUMENTS

| | | |
|---|---|---|
| WO | WO 2008/057950 A2 | 5/2008 |
| WO | WO 2012/018891 A2 | 2/2012 |

OTHER PUBLICATIONS

Kamgang-Youbi, et al, " Evidence of Temporal Post-Discharge Decontamination of Bacteria by Gliding Electric Discharges: Application to Hafnia alvei", Applied and Environmental Microbiology, vol. 73(15), Jun. 8, 2007, 4791-4796.

Kamgang-Youbi, et al, "Microbial Inactivation Using Plasma-Activated Water Obtained by Gliding Electric Discharges", Letters in Applied Microbiology, vol. 48(1), Jan. 1, 2009, 13-18.

Olofsson, et al., "N-Acetyl-L-Cysteine Affects Growth, Extracellular Polysaccharide Production, and Bacterial Biofilm Formation on Solid Surfaces", Applied and Environmental Microbiology, vol. 69(8), Aug. 1, 2003, 4814-4822.

Parry, et al., "Effect of N-acetylcysteine on Antibiotic Activity and Bacterial Growth in Vitro", Journal of Clinical Microbiology, American Society for Microbiology, vol. 5(1)1, Jan. 1, 1977, 58-61.

Burlica et al, "Organic Dye Removal From Aqueous Solution by Glidarc Discharges", Journal of Electrostatics, Nov. 2004, 62(4), 309-321.

Burlica, "Formation of Reactive Species in Gliding Arc Discharges With Liquid Water", Journal of Electrostatics, Jan. 2006, 64(1), 35-43.

Chen et al, "Inactivation of Aquatic Microorganisms by Low-Frequency AC Discharges", IEEE Transactions on Plasma Science, Feb. 2008, 36(1), 215-219.

Doubla, "Plasmachemical Decolourisation of Bromothymol Blue by Gliding Electric Discharge at Atmospheric Pressure", Dyes and Pigments, 2008, 77, 118-124.

Ikawa et al, "Effects of pH on Bacterial Inactivation in Aqueous Solutions due to Low-Temperature Atmospheric Pressure Plasma Application", Plasma Process. Polym. Jan. 2010, 7, 33-42.

International Patent Application No. PCT/US2011/046382: International Search report and The Written Opinion of the International Searching Authority, dated Dec. 16, 2011, 9 pages.

Marouf-Khelifa et al, "Reduction of Nitrite by Sulfamic Acid and Sodium Azide From Aqueous Solutions Treated by Gliding Arc Discharge", Separation and Purification Technology, Jul. 2006, 50(3), 373-379.

Moreau et al, "Gliding Arc Discharge in the Potato Pathogen *Erwinia carotovora* subsp. *atroseptica*: Mechanism of Lethal Action and Effect on Membrane-Associated Molecules", Applied and Environmental Microbiology, Sep. 2007, 73(18), 5904-5910.

Moussa et al, "Acidity Control of the Gliding arc Treatments of Aqueous Solutions: Application to Pollutant Abatement and Biodecontamination", Eur. Phys. J. Appl. Phys., Feb. 2005, 29, 189-199.

Naïtali et al, "Combined Effects of Long-Living Chemical Species during Microbial Inactivation Using Atmospheric Plasma-Treated Water", Applied and Environmental Microbiology, Nov. 2010, 76(22), 7662-7664.

Satoh et al, "Pulsed-Plasma Disinfection of Water Containing *Escherichia Coli*", Japanese Journal of Applied Physics, 2007, 46(3A), 1137-1141.

Shainsky, "Non-Equilibrium Plasma Treatment of Liquids, Formation of Plasma Acid", 2011, ispc-conference, 4 pages.

\* cited by examiner

| E. Coli cells washed twice with PBS | | | | |
|---|---|---|---|---|
| NAC (mM) | 0 | 2.5 | 5 | 10 |
| Cfu / mL | $3.0 \times 10^8$ | $3.1 \times 10^8$ | $2.1 \times 10^8$ | $1.2 \times 10^8$ |

FIGURE 3

| E. Coli cells NOT washed | | | | |
|---|---|---|---|---|
| NAC (mM) | 0 | 2.5 | 5 | 10 |
| Cfu / mL | $1.0 \times 10^8$ | $1.0 \times 10^8$ | $6.9 \times 10^7$ | $4.1 \times 10^7$ |

FIGURE 4

| NAC (mM) | 0 | 2.5 | 5 | 10 |
|---|---|---|---|---|
| Cfu / mL | $9.9 \times 10^7$ | $8.4 \times 10^7$ | $4.2 \times 10^7$ | $3.2 \times 10^6$ |

S. aureus cells washed twice with PBS

FIGURE 5

Pathogens (Planktonic)

Pathogens (Biofilm)

FIG. 16H
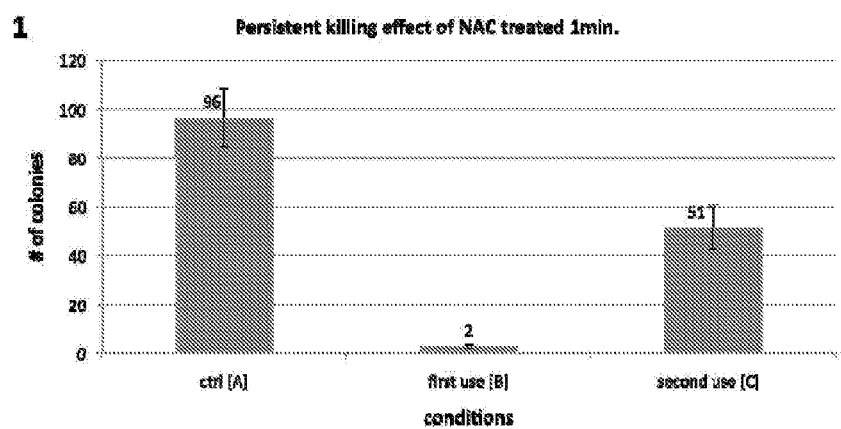
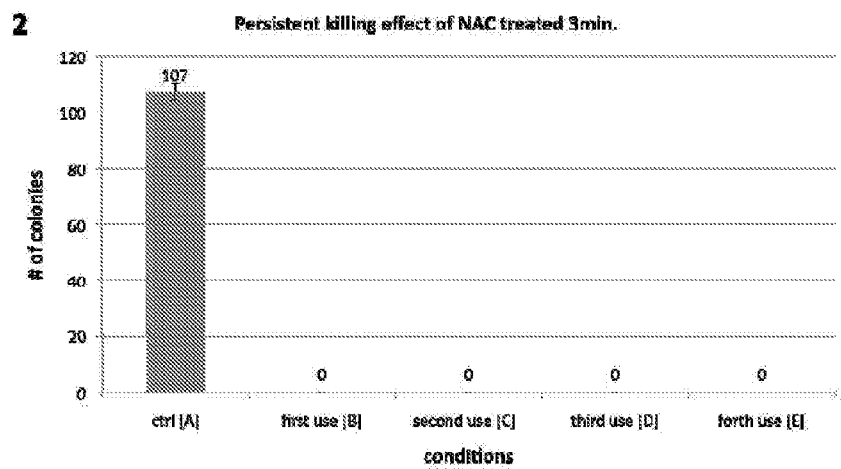

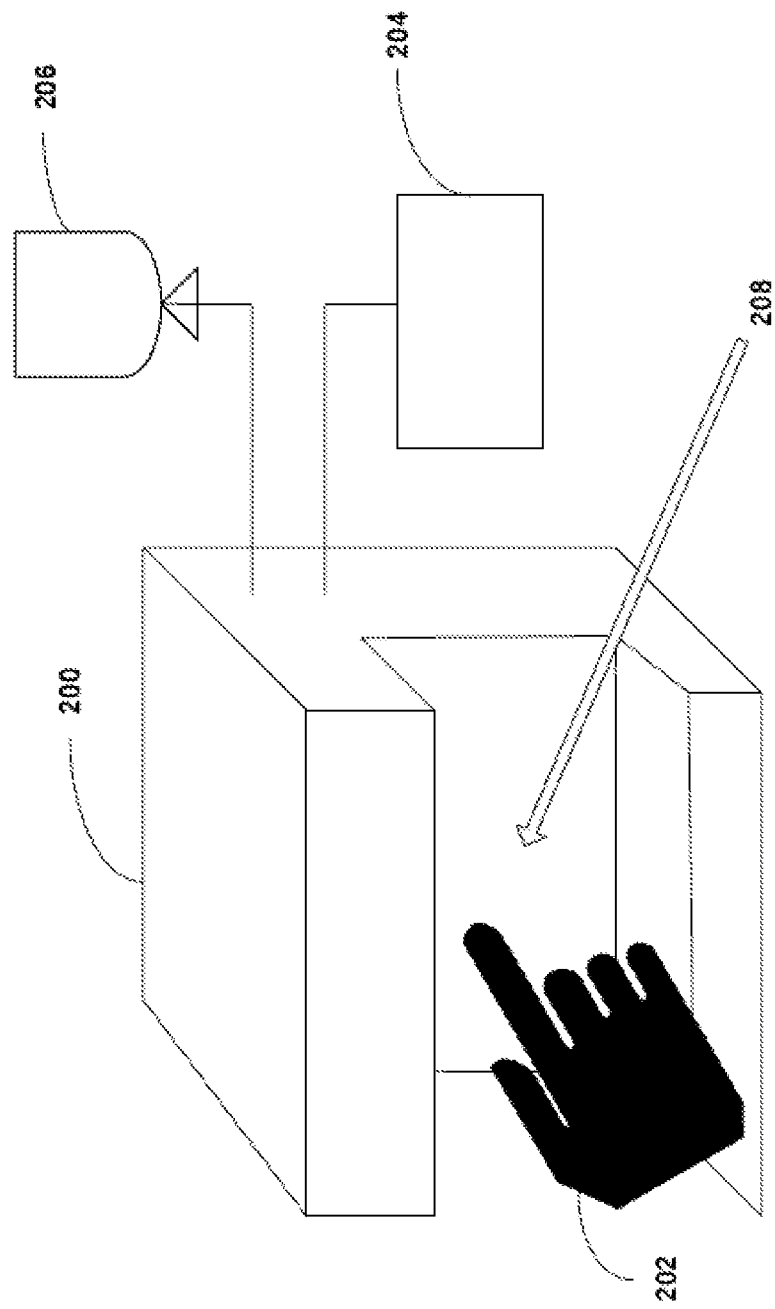

MATERIALS FOR DISINFECTION PRODUCED BY NON-THERMAL PLASMA

CROSS-REFERENCE TO RELATED APPLICATIONS

This application is the National Stage of International Application No. PCT/US2011/046382, filed Aug. 3, 2011, which claims the benefit of U.S. Provisional Application No. 61/370,392, filed Aug. 3, 2010, and U.S. Provisional Application No. 61/370,409, filed Aug. 3, 2010, the disclosures of which are incorporated herein by reference in their entireties.

TECHNICAL FIELD

Aspects of the disclosed subject matter are in the field of disinfection using plasma.

BACKGROUND

Plasma is an ionized gas. However, in addition to ions and electrons, plasma typically contains chemically active molecules as well as electronically excited atoms and molecules all of which do not remain in their active state for a long time (less than several seconds in most cases at atmospheric pressure) outside plasma. Recently, plasmas have been shown useful for disinfection and sterilization of materials, water, air, and living tissues. Current technologies include applying plasma itself or blowing active agents produced in plasma directly to the surface being sterilized to inactivate micro-organisms. In order to place the active agents in the plasma in direct contact with the surface, the device generating the plasma or a flow transporting mechanism (such as a tube) is placed in an appropriate position.

SUMMARY

The present invention is directed toward the use of plasma-treated materials as disinfecting agents.

Various embodiments of the present invention are directed to methods comprising contacting a fluid with plasma to form a disinfection composition; and contacting the disinfection composition with a surface, wherein said surface is at least partially disinfected upon contact with the disinfection composition.

Other embodiments provide methods comprising forming a disinfection composition by contacting fluid with a plasma, wherein the disinfection composition comprises a liquid and is capable of at least partially disinfecting a surface.

Still other embodiments provide disinfection compositions prepared by contacting a fluid with plasma, wherein the disinfection composition comprises a liquid and is capable of at least partially disinfecting a surface. In certain embodiments, these disinfection composition are provided on a woven or non-woven fabric.

Other embodiments provide the methods for drying these disinfection compositions to form disinfecting powders, as well as the disinfecting powders. Other embodiments provide for methods and compositions wherein the disinfecting powder compositions are reconstituted to form a liquid, aerosol, or both. In certain embodiments, these disinfecting powders are provided in the form of a kit, with instructions as to how to reconstitute the dry powders.

Some embodiments are directed to plasma-treated alginate gels, as wound bandages or dressings.

Some embodiments provide methods comprising contacting liquid with a non-thermal plasma to form a disinfection composition; and contacting a surface with the disinfection composition, wherein the surface is at least partially disinfected upon contact with the disinfection composition.

Other embodiments are directed to devices for at least partially disinfecting a human body part, comprising a power supply for generating a plasma; a plasma-treating chamber in which a fluid and plasma can be introduced to form a disinfection composition; a disinfection chamber for contacting a human body part or medical device with the disinfection composition, wherein the human body part is at least partially disinfected upon contact with the disinfection composition.

Some aspects of the present subject matter are directed to methods comprising placing organic molecules in a carrier material, such as but not limited to, liquid, gel, or powder, generating plasma, contacting the carrier material with the plasma itself or with plasma generated chemically active and electronically excited molecules and atoms to create a disinfection compound which includes the organic molecules modified as a result of exposure to plasma or plasma generated active species and placing a surface in contact with the disinfection compound to at least partially disinfect at least a portion of the surface or using the disinfecting compound inside another material to cause at least disinfection of the latter. The contact between gas phase plasma and the carrier material can occur in various ways including through generation of plasma within voids or bubbles inside the carrier material, through generation of plasma around aerosolized carrier material, through generating plasma on a boundary between gas and bulk carrier material, or through passing plasma generated active species past the carrier material which could be in bulk or aerosolized form.

The disinfection compound may be of various types of materials, including water and organic materials, as well as being in a gaseous, gelatinous or liquid state. Further, the disinfection compound may be an antioxidant, such as N-Acetyl Cysteine. It may be an amino acid such as Cysteine. In certain embodiments, the disinfection compound is dissolved in a liquid. Suitable liquids include saline, deionized water, phosphate buffered saline, or a combination thereof. The amount of organic material in the disinfection compound may vary. In certain embodiments, the organic material in the disinfection compound is at a concentration of at least about 2.5 mM. In other embodiments, the organic material in the disinfection compound is at a concentration of at least about 5 mM. In still other embodiments, the organic material in the disinfection compound, or composition, is at a concentration of at least about 10 mM.

In some examples, the gelatinous substance may be an alginate. Alginates are gelatinous substances obtained from certain seaweeds and used as stabilizers and water retainers in beverages, ice cream, ices, frozen custard, emulsions, desserts, baked goods, and confectionery ingredients.

Plasma employed to create the disinfection compound may be non-thermal plasma such as an atmospheric pressure dielectric barrier discharge, corona discharge or pulsed corona discharge. The plasma may have different intensities depending on the embodiment. In applying plasma to a surface of bulk carrier material the non-thermal plasma may have surface power density of at least about 0.1 $J/cm^2$, or at least about 0.5 $J/cm^2$, or at least about 1 $J/cm^2$, or at least about 5 $J/cm^2$.

Plasma may also be in the form of thermal plasma such as an arc. Mixed forms of plasma (plasma whose gas temperature varies dramatically over the extent of the ionized gas), such as a gliding arc discharge, may also be employed in some embodiments. Plasma intensity in such cases may also depend on the specific embodiment or specific end point application. Different types of plasma or active species from different forms of plasma can be applied sequentially to the carrier material to generate disinfection compound.

In certain embodiments, the surface contacted with the disinfection composition is a medical device. In other embodiments, the surface is a living tissue. Advantageously, the surface may be contacted with the disinfection composition remote from the non-thermal plasma. In some embodiments, the surface is contacted with the disinfection composition immediately after the disinfection composition is formed. For example, the surface may contact the disinfection composition in less than a minute after the disinfection composition is formed. The surface may be contacted with the disinfection composition in less than 10 seconds after the disinfection composition is formed. The surface may be contacted with the disinfection composition in less than 1 second after the disinfection composition is formed. The surface may be contacted with the disinfection composition in less than 0.1 second after the disinfection composition is formed.

In other embodiments, the surface is contacted with the disinfection composition a longer period of time after the disinfection composition is formed. Suitable periods of time include at least about 20 minutes, at least about 60 minutes, at least about 90 minutes, or at least about 120 minutes. The surface may be in contact with the disinfection composition for varying amounts of time. Suitable amounts of time include, for example, at least about 600 seconds, at least about 60 seconds, at least about 30 seconds, at least about 15 seconds, or at least about 5 seconds. It should be understood that the surface contact time may exceed 600 seconds. For example, an exemplary and non-limiting example may be that the disinfection composition is left on the surface for several days.

The extent to which the surface is disinfected may vary. In certain embodiments, the surface is at least about 50% disinfected upon contact with the disinfection composition. In other embodiments, the surface is at least 75% disinfected upon contact with the disinfection composition. Preferably, the surface is at least 90% disinfected upon contact with the disinfection composition. More preferably, the surface is at least 95% disinfected upon contact with the disinfection composition.

An additional aspect of the present subject matter is directed to a method comprising forming a disinfection composition by contacting water and/or an organic material with a non-thermal plasma. The disinfection composition may be a liquid. In certain embodiments, the disinfection composition may be an aerosol. In certain embodiments, the organic material is dissolved in a liquid. Suitable liquids include saline, deionized water, phosphate buffered saline, or a combination thereof. The amount of organic material in the disinfection composition may vary. In certain embodiments, the organic material in the disinfection composition is at a concentration of at least about 2.5 mM. In other embodiments, the organic material in the disinfection composition is at a concentration of at least about 5 mM. In still other embodiments, the organic material in the disinfection composition is at a concentration of at least about 10 mM.

An additional aspect of the present subject matter is directed to a disinfection composition comprising an organic material contacted by a non-thermal plasma. The disinfection composition may be a liquid. In certain embodiments, the disinfection composition is an aerosol. The organic material may be an antioxidant, preferably N-Acetyl Cysteine. The organic material may be dissolved in a liquid. Suitable liquids include, for example, saline, deionized water, phosphate buffered saline, or a combination thereof.

A further aspect of the present subject matter is directed to a product formed by the process of contacting an organic material with a non-thermal plasma. The organic material may be an antioxidant, preferably N-Acetyl Cysteine. In certain embodiments, the organic material is dissolved in a liquid. Suitable liquids include, for example, saline, deionized water, phosphate buffered saline, or a combination thereof.

In certain other embodiments the present subject matter is directed to a disinfection composition comprising an aqueous liquid contacted by a non-thermal plasma. This aqueous liquid may be water and may contain organic material or may be free of added organic material. The aqueous liquid may be water which optionally contained inorganic salts, for example a phosphate buffer.

In certain embodiments, the non-thermal plasma is an atmospheric pressure dielectric barrier discharge. The plasma intensity may be at least about $0.1$ $J/cm^2$, or at least about $0.5$ $J/cm^2$, or at least about $1$ $J/cm^2$, or at least about $5$ $J/cm^2$.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The foregoing and other aspects of the present subject matter will become apparent from the following detailed description of the subject matter when considered in conjunction with the accompanying drawings. For the purpose of illustrating the subject matter, there is shown in the drawings embodiments that are presently preferred, it being understood, however, that the subject matter is not limited to the specific instrumentalities disclosed. The drawings are not necessarily drawn to scale. In the drawings:

FIG. 3 shows the response of NAC alone on *Escherichia coli* cells upon incubation for 30 minutes at room temperature wherein the cells were washed twice with phosphate buffered saline;

FIG. 4 shows the response of NAC alone on *Escherichia coli* cells upon incubation for 30 minutes at room temperature wherein the cells were not washed;

FIG. 5 shows the response of NAC alone on *Staphylococcus aureus* cells upon incubation for 30 minutes at room temperature wherein the cells were washed twice with phosphate buffered saline;

FIG. 16H shows the effects of killing persistence of plasma treated NAC solutions on 10$^7$CFU/mL colonies of *E. coli*, 15 minute hold times.

FIGS. 26A, C, & D shows the antimicrobial effect of reconstituted NAC powders derived from plasma-treated solutions. FIG. 26B shows the antimicrobial effect of plasma-treated NAC powders.

FIG. 27 is an exemplary device that may be used to sterilize or disinfect the arm or hand of a person.

DETAILED DESCRIPTION OF ILLUSTRATIVE EMBODIMENTS

Figure 1:
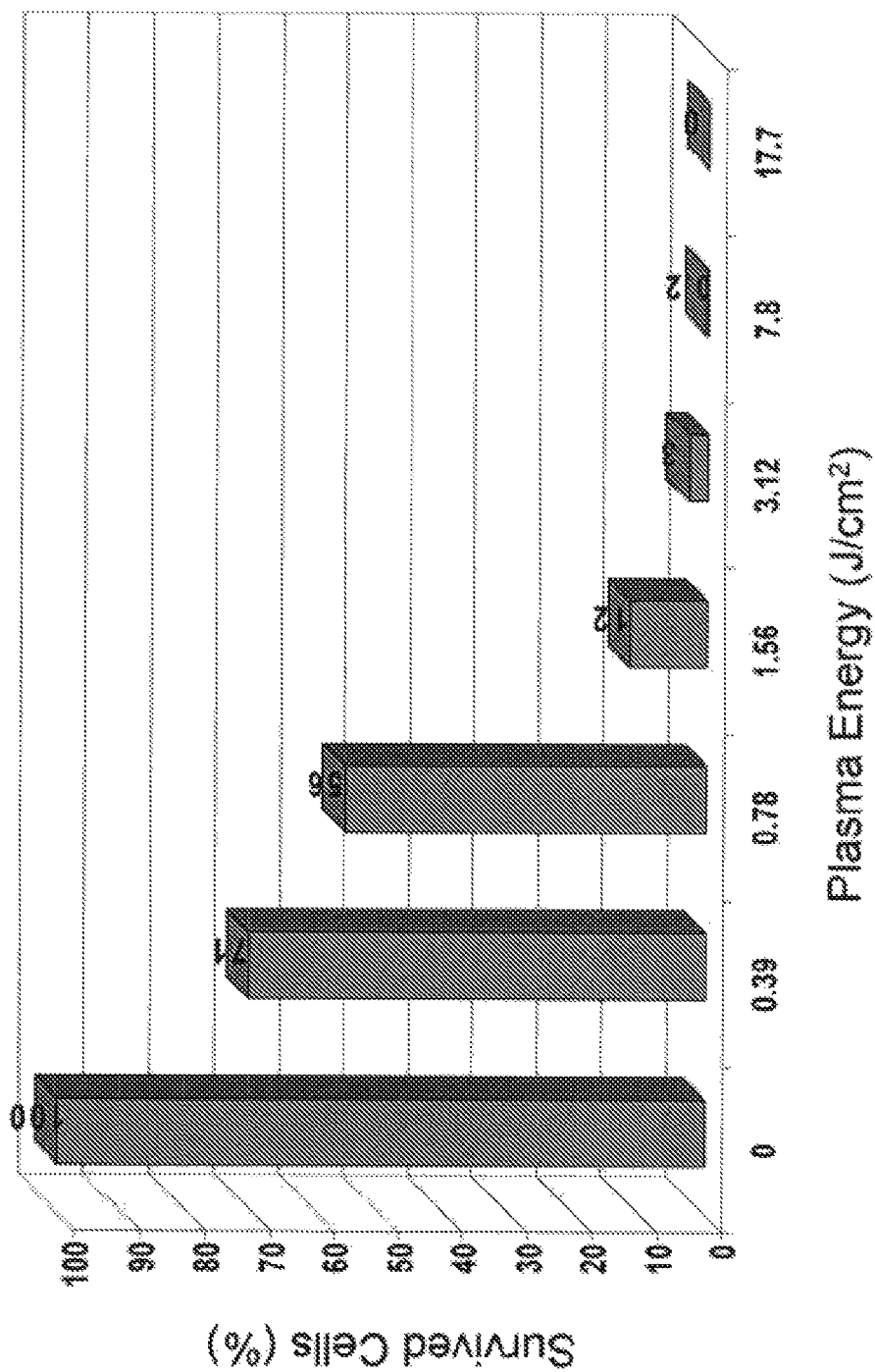
FIG. 1 shows the percentage of surviving *Staphylococcus aureus* cells after being contacted with plasma at different plasma energies from a dielectric barrier discharge generated at 500 Hz (0.13 $W/cm^2$)

The present invention is directed to use of plasma as a disinfecting agent. Various embodiments of the present invention are directed to methods comprising contacting a fluid with plasma to form a disinfection composition; and contacting the disinfection composition with a surface, wherein said surface is at least partially disinfected upon contact with the disinfection composition.

Other embodiments provide methods comprising forming a disinfection composition by contacting fluid with a plasma, wherein the disinfection composition comprises a liquid and is capable of at least partially disinfecting a surface.

Still other embodiments provide disinfection compositions prepared by contacting a fluid with a plasma, wherein the disinfection composition comprises a liquid and is capable of at least partially disinfecting a surface. In certain embodiments, these disinfection composition are provided on a woven or non-woven fabric.

Other embodiments provide the methods for drying these disinfection compositions to form disinfecting powders, as well as the disinfecting powders. Other embodiments provide for methods and compositions wherein the disinfecting powder compositions are reconstituted to form a liquid, aerosol, or both. In certain embodiments, these disinfecting powders are provided in the form of a kit, with instructions as to how to reconstitute the dry powders.

Some embodiments are directed to plasma-treated alginate gels, as wound bandages or dressings.

Some embodiments provide methods comprising contacting liquid with a non-thermal plasma to form a disinfection composition; and contacting a surface with the disinfection composition, wherein the surface is at least partially disinfected upon contact with the disinfection composition.

Other embodiments are directed to devices for at least partially disinfecting a human body part, comprising a power supply for generating a plasma; a plasma-treating chamber in which a fluid and plasma can be introduced to form a disinfection composition; a disinfection chamber for contacting a human body part or medical device with the disinfection composition, wherein the human body part is at least partially disinfected upon contact with the disinfection composition.

The present subject matter may be understood more readily by reference to the following detailed description taken in connection with the accompanying figures and examples, which form a part of this disclosure. It is to be understood that this subject matter is not limited to the specific devices, methods, applications, conditions or parameters described and/or shown herein, and that the terminology used herein is for the purpose of describing particular embodiments by way of example only and is not intended to be limiting of the claimed subject matter.

Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to methods of using, the compositions used in those methods, as well as the methods of manufacturing the compositions used in those methods.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Finally, while an embodiment may be described as part of a series of steps or part of a more general composition or structure, each said step may also be considered an independent embodiment in itself.

Plasmas, referred to as the "fourth state of matter," are ionized gases having at least one electron that is not bound to an atom or molecule. In recent years, plasmas have become of significant interest to researchers in fields such as organic and polymer chemistry, fuel conversion, hydrogen production, environmental chemistry, biology, and medicine, among others. This is, in part, because plasmas offer several advantages over traditional chemical processes. For example, plasmas can generate much higher temperatures and energy densities than conventional chemical technologies; plasmas are able to produce very high concentrations of energetic and chemically active species; and plasma systems can operate far from thermodynamic equilibrium, providing extremely high concentrations of chemically active species while having a bulk temperature as low as room temperature.

Plasmas are generated by ionizing gases using any of a variety of ionization sources. Depending upon the ionization source and the extent of ionization, plasmas may be characterized as either thermal or non-thermal. Thermal and non-thermal plasmas can also be characterized by the temperature of their components. Thermal plasmas are in a state of thermal equilibrium, that is, the temperature of the free electrons, ions, and heavy neutral atoms are approximately the same. Non-thermal plasmas, or cold plasmas, are far from a state of thermal equilibrium; the temperature of the free electrons is much greater than the temperature of the ions and heavy neutral atoms within the plasma.

The initial generation of free electrons may vary depending upon the ionization source. With respect to both thermal and non-thermal ionization sources, electrons may be generated at the surface of the cathode due to a potential applied across the electrode. In addition, thermal plasma ionization sources may also generate electrons at the surface of a cathode as a result of the high temperature of the cathode (thermionic emissions) or high electric fields near the surface of the cathode (field emissions).

The energy from these free electrons may be transferred to additional plasma components, providing energy for additional ionization, excitation, dissociation, etc. With respect to non-thermal plasmas, the ionization process typically occurs by direct ionization through electron impact. Direct ionization occurs when an electron of high energy interacts with a valence electron of a neutral atom or molecule. If the energy of the electron is greater than the ionization potential of the valence electron, the valence electron escapes the electron cloud of the atom or molecule and becomes a free electron according to:

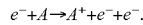

$$e^- + A \rightarrow A^+ + e^- + e^-.$$

As the charge of the ion increases, the energy required to remove an additional electron also increases. Thus, the energy required to remove an additional electron from $A^+$ is greater than the energy required to remove the first electron from A to form $A^+$. A benefit of non-thermal plasmas is that because complete ionization does not occur, the power to the ionization source can be adjusted to increase or decrease ionization. This ability to adjust the ionization of the gas provides for a user to "tune" the plasma to their specific needs.

An exemplary thermal plasma ionization source is an arc discharge. Arc discharges have been otherwise used for applications such as metallurgy, metal welding and metal cutting and are known per se. Arc discharges are formed by the application of a potential to a cathode, and arc discharges are characterized by high current densities and low voltage drops. Factors relevant to these characteristics are the usually short distance between the electrodes (typically a few millimeters) and the mostly inert materials of the electrodes (typically, carbon, tungsten, zirconium, silver, etc). The majority of electrons generated in arc discharges are formed by intensive thermionic and field emissions at the surface of the cathode. That is, a much larger number of the electrons are generated directly from the cathode as opposed to secondary sources such as excited atoms or ions. Because of this intense generation of electrons at the cathode, current at the cathode is high, which leads to Joule heating and increased temperatures of the cathodes. Such high temperatures can result in evaporation and erosion of the cathode. The anode in arc discharges may be either an electrode having a composition identical or similar to the cathode or it may be another conductive material. For example, the anode in arc discharges used in metal welding or cutting is the actual metal to be welded or cut. Typical values for parameters of thermal arc discharges can be seen in Table 1:

TABLE 1

Arc Discharge Parameters

| Parameters of a Thermal Arc Discharge | Typical Values |
|---|---|
| Gas Pressure | 0.1 to 100 atm |
| Arc Current | 30 A to 30 kA |
| Cathode Current Density | $10^4$ to $10^7$ A/cm$^2$ |
| Voltage | 10 to 100 V |
| Power per unit length | ~1 kW/cm |
| Electron Density | $10^{15}$ to $10^{19}$ cm$^{-3}$ |
| Gas Temperature | 1 to 10 eV |
| Electron Temperature | 1 to 10 eV |

Although thermal plasmas are capable of delivering extremely high powers, they have several drawbacks. In addition to the electrode erosion problems discussed above, thermal plasmas do not allow for adjusting the amount of ionization, they operate at extremely high temperatures, and they lack efficiency.

Non-thermal plasma ionization sources have alleviated some of the above-mentioned problems. Exemplary ionization sources for non-thermal plasmas include glow discharges, dielectric barrier discharges, and gliding arc discharges, among others. In contrast to thermal plasmas, non-thermal plasmas provide for high selectivity, high energy efficiencies, and low operating temperatures. In many non-thermal plasma systems, electron temperatures are about 10,000 K while the bulk gas temperature may be as cool as room temperature.

A glow discharge is a plasma source that generates a non-equilibrium plasma between two electrodes under a direct current. There are several types of glow discharges; a common one is the fluorescent light. This glow discharge is established in a long tube with a potential difference applied between an anode at one end of the tube and a cathode at the other end. The tube is filled with an inert or reactive gas often under pressure. Due to the potential difference between the electrodes, electrons are emitted from the cathode and accelerate toward the anode. The electrons collide with gas atoms in the tube and form excited species. These excited species decay to lower energy levels through the emission of light (i.e., glow). The ionized species generated by the collision of electrons with gas atoms travel toward the cathode and release secondary electrons, which are then accelerated toward the anode. This generation of electrons, referred to as secondary emission, is in contrast to the intensive formation of electrons at the surface of the cathode in thermal plasma generation. Typical parameters of a glow discharge as described above are shown in Table 2:

TABLE 2

Parameters of Glow Discharge

| Parameters of a Glow Discharge | Typical Values |
| --- | --- |
| Discharge Tube Radius | 0.3 to 3 cm |
| Discharge Tube Length | 10 to 100 cm |
| Plasma Volume | About 100 $cm^3$ |
| Gas Pressure | 0.03 to 30 Torr |
| Voltage Between Electrodes | 100 to 1000 V |
| Electrode Current | $10^{-4}$ to 0.5 A |
| Power Level | ~ 100 W |

Dielectric barrier discharge (DBD) may be generated using an alternating current at a frequency of from about 0.5 kHz to about 500 kHz between a high voltage electrode and a ground electrode. In addition, one or more dielectric barriers are placed between the electrodes. DBDs have been employed for over a century and have been used for the generation of ozone in the purification of water, polymer treatment (to promote wettability, printability, adhesion), and for pollution control. DBDs prevent spark formation by limiting current between the electrodes.

Several materials can be utilized for the dielectric barrier. These include glass, quartz, and ceramics, among others. The clearance between the discharge gaps is typically between about 0.1 mm and several centimeters. The required voltage applied to the high voltage electrode varies depending upon the pressure and the clearance between the discharge gaps. For a DBD at atmospheric pressure and a few millimeters between the gaps, the voltage required to generate a plasma is typically about 10 kV. In certain embodiments, the ground electrode of the DBD may be an external conductive object, such as a human body. This is known as floating-electrode DBD (FE-DBD). FE-DBD has recently been utilized in medical applications.

Figure 2:
FIG. 2 shows the percentage of surviving *Escherichia coli* cells after being contacted with plasma at different energies.

Aspects of the present subject matter are directed to contacting an organic or aqueous-based material with a non-thermal plasma to form a disinfection composition. It should be noted that, as discussed previously, the presently disclosed subject matter is not limited to any one type of plasma. The following description is based upon the use of non-thermal plasma for descriptive purposes only and is not intended to limit the scope of the presently disclosed subject matter to non-thermal plasma. The disinfection composition may be a liquid and the surface may be contacted with the disinfection solution to at least partially disinfect the surface. Plasmas have been found to be useful for disinfection and sterilization of materials such as water, air, medical devices and tissues. Traditionally, a plasma is applied directly to the material for disinfection/sterilization ("direct plasma sterilization"). In some cases UV (Ultra-Violet radiation) produced in the plasma is the active agent responsible for inactivation of micro-organisms. In other cases, plasma produced ozone or radicals such as OH or NO are the active disinfecting agents. Intense sound waves produced by plasma in liquids are also suspected to kill bacteria. FIGS. 1 and 2 show the percentage of surviving bacteria cells after a traditional direct plasma sterilization. Depending upon the bacteria, at a plasma energy of 0.78 $J/cm^2$, approximately 50% of the bacteria cells survive the plasma treatment. In order to accomplish lower percentages of surviving cells, high plasma energies must be applied. Use of higher plasma energies in undesirable because of increases costs and the potential to damage surrounding areas of the material.

In certain embodiments, the non-thermal plasma, is a dielectric barrier discharge (DBD). A DBD may be generated using an alternating current at a frequency of from about 0.5 kHz to about 500 kHz between a high voltage electrode and a ground electrode. It should be noted that in certain configurations, a single pulse may be used. Therefore, the present subject matter may be preferably used in applications ranging from a single pulse to about 500 kHz. In addition, one or more dielectric barriers are placed between the electrodes. Exemplary surface power density outputs may be between about 0.001 $Watt/cm^2$ to about 100 $Watt/cm^2$.

Various materials can be utilized for the dielectric barrier. These include plastic, glass, quartz, and ceramics, among others. The clearance between the discharge gaps is typically between about 0.01 mm and several centimeters. The required voltage applied to the high voltage electrode varies depending upon the pressure and the clearance between the discharge gaps. For a DBD at atmospheric pressure and a few millimeters between the gaps, the voltage required to generate a plasma may vary, but in some configurations, is about 10 kV.

In certain embodiments, the plasma may be generated having an energy of at least about 0.1 $J/cm^2$. In other embodiments, the plasma may have an energy of at least about 0.5 $J/cm^2$ or at least about 1 $J/cm^2$ or at least about 5 $J/cm^2$. The energy of the plasma may vary depending upon the surface being treated, the extent of disinfection required, and the type and amount of organic material in the disinfection composition.

Aspects of the present subject matter offer alternative methodologies for plasma based disinfection and sterilization. As used herein, the terms "disinfect," "disinfecting," or the like refer to the ability or render pathogens less active, or to kill, inactivate, inhibit the growth, or otherwise render pathogens innocuous or less active, where pathogens include bacteria, microbes, fungi, or yeasts. Exemplary, albeit non-limiting, pathogens include *Acinetobacter baumannii, Escherichia coli, Enterococcus faecalis, Pseudomonas aeruginosa, Staphylococcus aureus* (including drug resistant strains such as any variety of MRSA), *Staphylococcus epidermidis, Candida albicans,* and *Candida glabrata*. Disinfection can be quantified using standard tests, including Safranin assay, LIVE/DEAD BacLight BacterialViability Assay, or XTT assay.

A benefit of aspects of the present subject matter compared to traditional direct plasma sterilization techniques is the ability to apply the disinfection composition remote from the plasma source. For example, the material to be plasma-treated may be contacted with a plasma to form a disinfection composition and the disinfection composition may be subsequently transported to another location for contacting with a surface. For example, the disinfection composition may be formed and transported to a different location within a laboratory of surgical room, or it may be transported to an entirely different building. Thus, in certain embodiments, the surface may not be contacted with the disinfection composition for a period of time after the disinfection composition is formed. In certain embodiments, the period of time may be at least about 20 minutes, at least about 30 minutes or at least about 60 minutes, or at least about 90 minutes, or at least about 120 minutes.

In other embodiments, a surface may be contacted with the disinfection composition immediately after the disinfection composition is formed. For example, the disinfection composition may be formed at a "disinfection station" wherein surfaces, such as medical devices and other components may be disinfected, for example, near or in an operating room or hospital. In certain embodiments, the surface is contacted with the disinfection composition in less than about 1 minute after the disinfection composition is formed, or for example, in less than about 10 seconds, or in less than about 1 second, or in less than about 0.1 seconds.

The material to be plasma-treated may be contacted by a plasma for different periods of time. This period of time may vary depending upon factors such as the material to be plasma-treated, the type of plasma, and the plasma intensity among other. In certain embodiments, the material to be plasma-treated may be contacted with the plasma for at least about 10 seconds, or at least about 60 seconds, or for at least about 90 seconds. Once a surface is contacted with a disinfection material, the disinfection material may remain in contact with the surface for a period of time that may be referred to as a "hold time." In certain embodiments, the hold time may be at least about 5 seconds, or at least about 30 seconds, or at least about 60 seconds, or at least about 600 seconds.

The extent of disinfection depends upon factors such as the type and amount of plasma-treated material, plasma energy, and exposure time, among others. In certain embodiments, the surface is at least about 50% disinfected upon contact with the disinfection composition, or, for example, at least about 75%, or, for example, at least about 90%, or, for example, at least about 95% disinfected.

In some embodiments, the disinfecting composition comprise plasma treated aqueous or organic fluids (e.g., ethanol or isopropanol) or other organic molecules (in solution, or as gels or solids), which then may act as the active antimicrobial agents. The organic molecules may be contacted by the plasma to create a disinfection composition for the disinfection of a surface. In certain embodiments, the organic molecule may be dispersed in a liquid. Suitable liquids include saline, deionized water, and phosphate buffered saline (PBS), among others. A plasma may be created electrically in the gas phase near a gas/liquid interface. The organic molecule dispersed in the liquid may be contacted by the plasma to form a liquid disinfection composition. This liquid can, for example, be used to wash living tissues as well as other material surfaces for the purposes of disinfection or sterilization.

A liquid disinfection composition provides benefits over a traditional direct plasma sterilization or gaseous composition. For example, a liquid disinfection composition may be particularly suited for disinfection of devices having inner cavities difficult to reach with a plasma or gas disinfection composition. For example, a liquid disinfection composition may be used to disinfect the inside of devices such as intravenous tubing, heplocks, intravenous catheters, urinary catheters, wounds, or other indwelling medical devices. Additionally, a liquid disinfection composition may provide for visualization that an entire surface has been contacted with the disinfection solution. In this latter regard, the liquid disinfecting composition may also include a colorant or other detectable additive, provided the additive does not interfere with the disinfectant character of the plasma-treated liquid in any appreciable way (i.e., the plasma-treated liquid provides at least a portion the activity associated with a comparable composition without the additive).

In certain embodiments, the disinfection composition may be aerosolized. An aerosolized disinfection composition may provide for a thin coating of the disinfection composition over an entire surface. Exemplary uses may be for the disinfection/sterilization of medical devices or other components used in a medical situation, such as, an operating room. In yet other embodiments, the disinfection composition may be used to charge a nebulizer for the treatment/ disinfection of airways of an individual with respiratory diseases or infections such as cystic fibrosis or pneumonias.

Figure 5A:
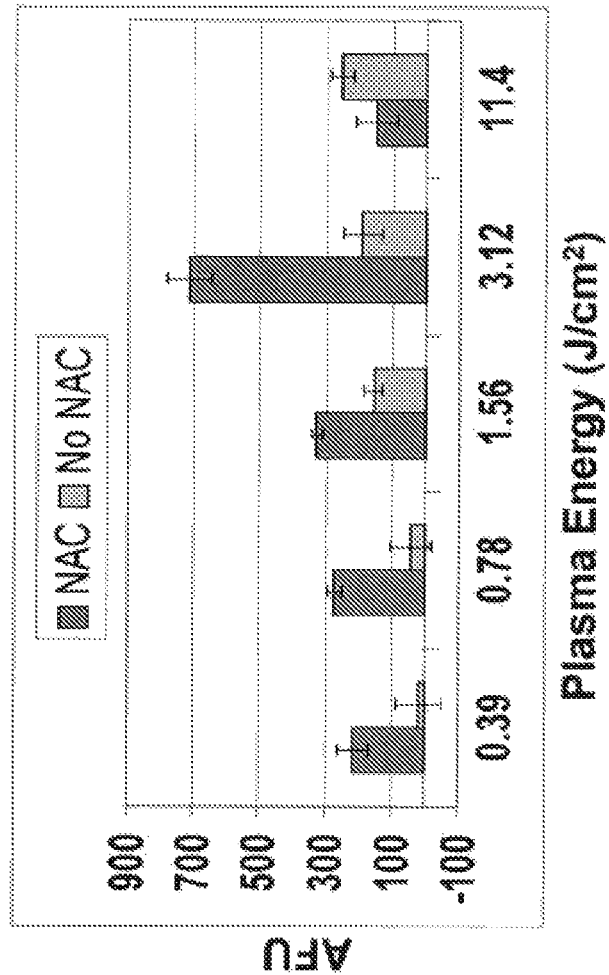
FIG. 5A shows a comparison of membrane potential between cells contacted with traditional direct plasma sterilization and plasma contacted NAC composition at varying plasma energies.

Various organic molecules may be suitable for the present subject matter. In a preferred embodiment, the organic molecule is an antioxidant. Suitable antioxidants include, for example, N-Acetyl Cysteine (NAC), ascorbic acid, glutathione, lipoic acid, uric acid, carotenes, α-tocopherol, carotenes, ubiquinol, and melatonin, among others. In a more preferred embodiment, the organic molecule is NAC. NAC is known to have antioxidant activity for humans providing protection against often harmful oxidative stress. It is also known to have some anti-microbial activity (FIGS. 3-5).

Among plasma-treated fluids, N-acetyl-cysteine solution stood out as a powerful antibacterial and antifungal agent. In certain embodiments, such fluids can disinfect (as evidenced by their ability to inactivate biofilms) *Acinetobacter baumannii, Escherichia coli, Enterococcus faecalis, Pseudomonas aeruginosa, Staphylococcus aureus* (including drug resistant strains such as any variety of MRSA), *Staphylococcus epidermidis, Candida albicans*, and *Candida glabrata*. In various embodiments, this disinfection can occur in less than 60, 45, 30, 15, 10, or 5 minutes of holding/contact time. In other embodiments, plasma-treated N-acetyl-cysteine solution are extremely stable, capable of exhibiting the equivalent of more than 6 months, or 1 or 2 years of shelf life at temperatures of 50° C. See, for example, the results shown below in the section, Experiments With Added Organic Materials—Series 2.

In other embodiments, the material to be activated by the non-thermal plasma is an alginate or other gelatinous material. Alginates are gelatinous substances obtained from certain seaweeds and used as stabilizers and water retainers in beverages, ice cream, ices, frozen custard, emulsions, desserts, baked goods, and confectionery ingredients. Alginic acid is a polysaccharide complex built from mannuronic acid units. Salts such as iron, magnesium and ammonium alginates form viscous solutions. Alginates hold large amounts of water and are useful as thickeners, stabilizers, and gelling, binding and emulsifying agents in ice-cream, synthetic cream etc. Alginates such as pure sodium alginate and potassium alginate, with low calcium content, create firm, fairly heat stable gels. Sodium alginate is available from cold storage with top gel strength, and white color (food grade) and produces varying viscosities. Sodium alginate is also used as gum and edible films by food industries. In presence of calcium salts it gives thermally irreversible gels. Major Monosaccharides are D-mannuronic acid, L-gluluronic acid and the anionic seaweed polysaccharides are often linear polymer of D-mannuronic acid and L-guluronic acid. Since 1983 the Alginates have been used as food ingredients, and the Food and Drug administration (FDA) has been pursuing tests for its safety. Alginate is obtained commercially from three genera of the marine brown algae, Phaeophyceae (*Macrocystis pyrifera, Laminaria digitata*, and *Laminaria saccharina*). The alginate molecule is a linear polysaccharide consisting of chains of repeating (D)-mannuronic acid (M blocks), (L)-guluronic acid (G blocks), and a combination of the two (MG blocks). Each type of chain is present in a specific ratio (M:G ratio) depending upon the species of algae. This ratio determines the characteristics of the gel, with G blocks capable of forming stronger, more brittle gels with good heat stability whereas high M content produces weaker more-elastic gels.

Sodium alginate is soluble in water. However, when the sodium is replaced with calcium, the ionic bond with calcium cross-links the polymer chains resulting in an insoluble gel. This gel is the basis for a variety of wound dressings. Other dressings are created using small fibers of calcium alginate that are applied as a paste or are pressed or woven to form a stronger fabric, and others are produced from freeze-dried alginate.

Using the presently disclosed subject matter, alginates may also be used in wound dressings. Currently available dressing material is hard and sticks to wounded dressed area and causes injury to healing granulation tissues when removed. Furthermore it is impregnated with chemicals or antibiotic-like antimicrobial agents (having a short lived effect). In some applications, an alginate activated according to the presently disclosed subject matter may be softer and more flexible with good moisture retention capabilities making it very easy to remove when dressings are changed. The Alginate gels or gels posessing similar properties when treated with non-thermal (DBD) plasma may simultaneously inhibit micribal growth and improve healing.

For example, the results of experiments described below (see Experiments with Alginate Gels—Series 1 and Series 2, below) demonstrate that calcium alginate gels treated by exposure to non-thermal plasma have the potential to be clinically useful wound dressings based on their broad spectrum of antimicrobial activity. They are a viable alternative to silver-containing dressings because of the faster rate of killing. This is important because of the potential for bacteria to develop resistance to slower-acting agents. With regard to silver, the fastest rate of kill quoted in the literature is 30 minutes, and as long as 24 hours. *E coli* reproduces about every 20 minutes (depending on the strain) correlating to ~$10^{21}$ colonies over 24 hours. Each new generation produced in an environment with a constant level of antibiotic has the potential to select for mutations that confer resistance. The chlorhexidine-containing dressing used for comparison in this study acts far more rapidly than silver, and chlorhexidine in solution has been shown to have 3.5-log reduction in *E coli* after only 30 seconds. While the plasma-treated gels do not act this quickly, the 10-minute killing time demonstrated is shorter than the average reproductive cycle of bacteria and is therefore likely not to lead to the development of resistance.

In various embodiments, the present invention includes those alginate gels which exhibit the disinfectant characteristics, including those described herein. Such gels include gels such as those prepared by the methods described herein. Further, use of these gels to disinfect surfaces and the methods of using these gels treated with plasma according to these conditions are also embodiments of the present invention.

In certain embodiments, the alginate gels of the present compositions or the methods derived from the gels described in previous paragraphs. These gels may further comprise least one of the organic materials described elsewhere within this specification or may be free of such organic materials. Likewise, these gels may comprise inorganic salts such as described herein, or may be free of any added inorganic salts or buffers.

In certain embodiments, the disinfecting alginate gels are prepared by exposing the gels to plasmas having energies of at least about 0.2 $J/cm^2$, at least about 0.4 $J/cm^2$, at least about 0.6 $J/cm^2$, at least about 0.8 $J/cm^2$, at least about 1 $J/cm^2$, at least about 1.5 $J/cm^2$, at least about 2 $J/cm^2$, at least about 3 $J/cm^2$, at least about 4 $J/cm^2$, at least about 5 $J/cm^2$, at least about 8 $J/cm^2$, at least about 10 $J/cm^2$, at least about 12 $J/cm^2$, at least about 14 $J/cm^2$, at least about 16 $J/cm^2$, at least about 18 $J/cm^2$, at least about 20 $J/cm^2$, or at least about 24 $J/cm^2$.

In certain embodiments, these gels and methods are capable of killing the pathogens described above, and including *Escherichia coli, Staphylococcus aureus, Staphylococcus epidermidis, Acetinobacter baumanii, Candida albicans,* and *Candida glabrata*. In other independent embodiments, these gels and methods are capable of at least partially (including completely) sterilizing surfaces (inactivating pathogens) described herein within 5 secs, 10 secs, 30 secs, 1 min, 3 min, 5 min, 10 min, and 30 minutes of contacting the plasma treated gels and the pathogens.

In other independent embodiments, the gels and methods are capable of maintaining at least a portion of their ability to inactivate pathogens (antimicrobial activity) for periods of 0.5, 1, 2, 4, 6, 8, 10, 12, or 24 hours, 1, 2, 3, 4, 5, or 6 days, 1, 2, 3, 4, 5, or 6 weeks after exposure to plasma treatment.

Figure 6:
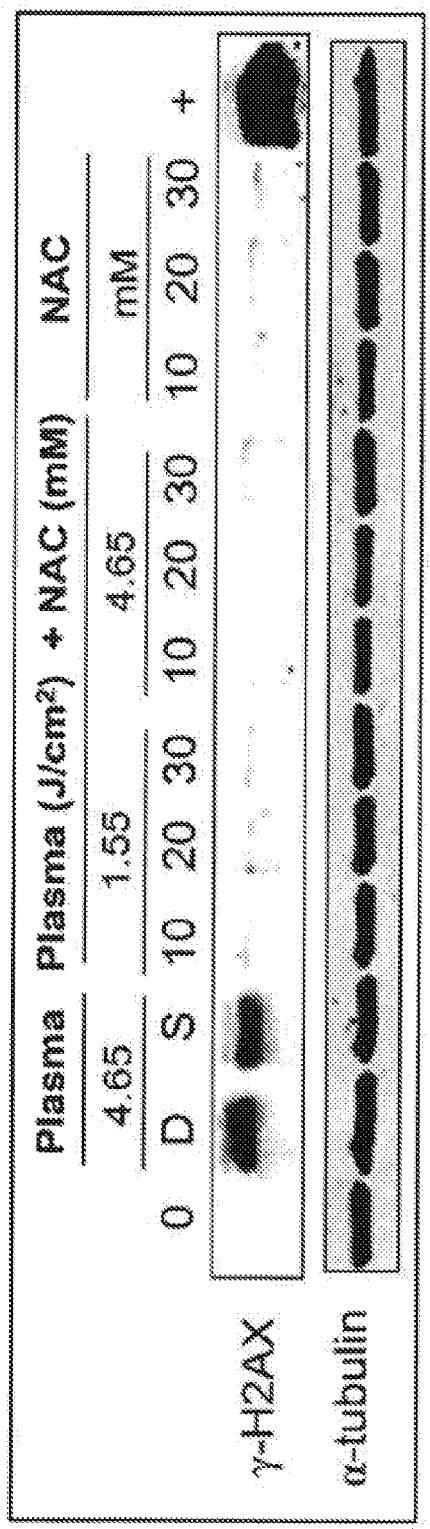
FIG. 6 shows a gel electrophoresis comparison of disinfection with traditional direct plasma sterilization, the application of NAC only, and the application of an exemplary disinfection composition.
Figure 7:
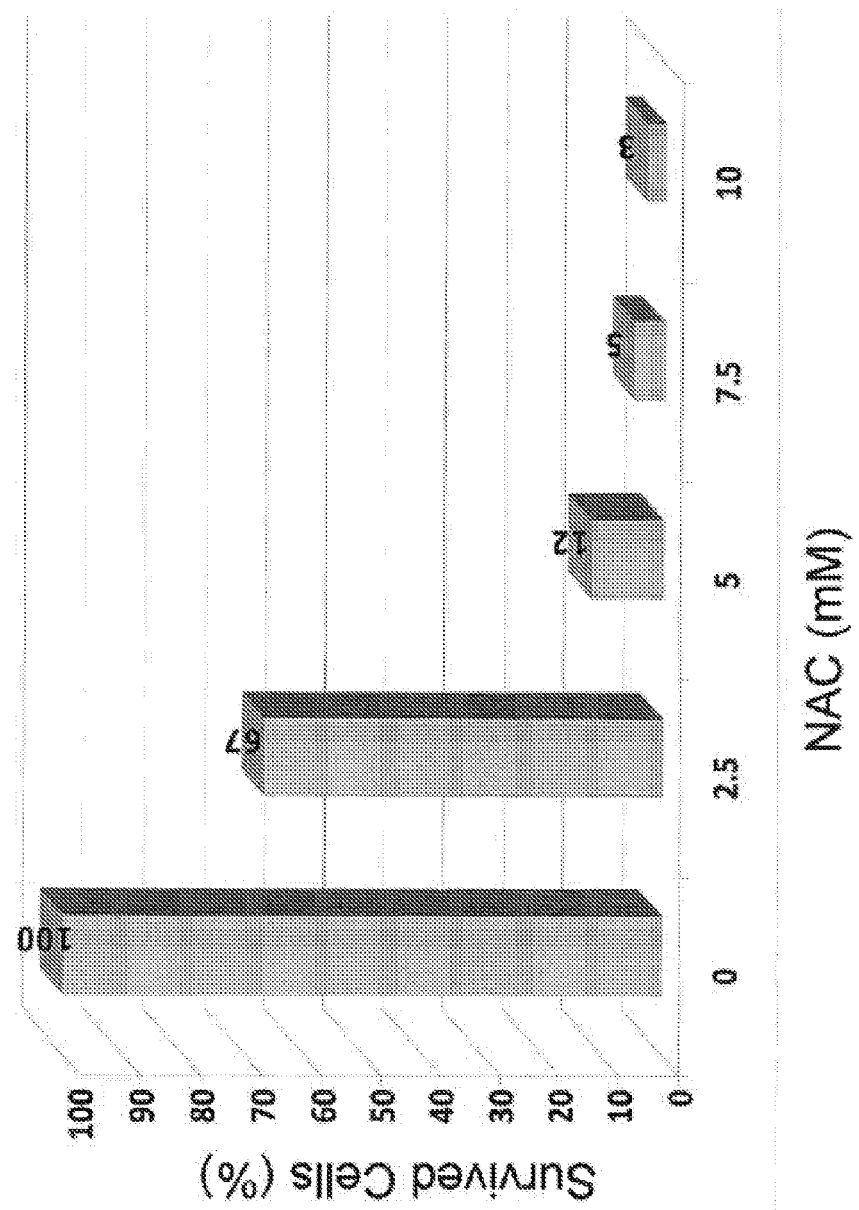
FIG. 7 shows the percentage of surviving *Escherichia coli* cells after being contacted with exemplary disinfection compositions comprising different concentrations of NAC contacted with a plasma at an energy of 0.78 J/cm$^2$.
Figure 8:
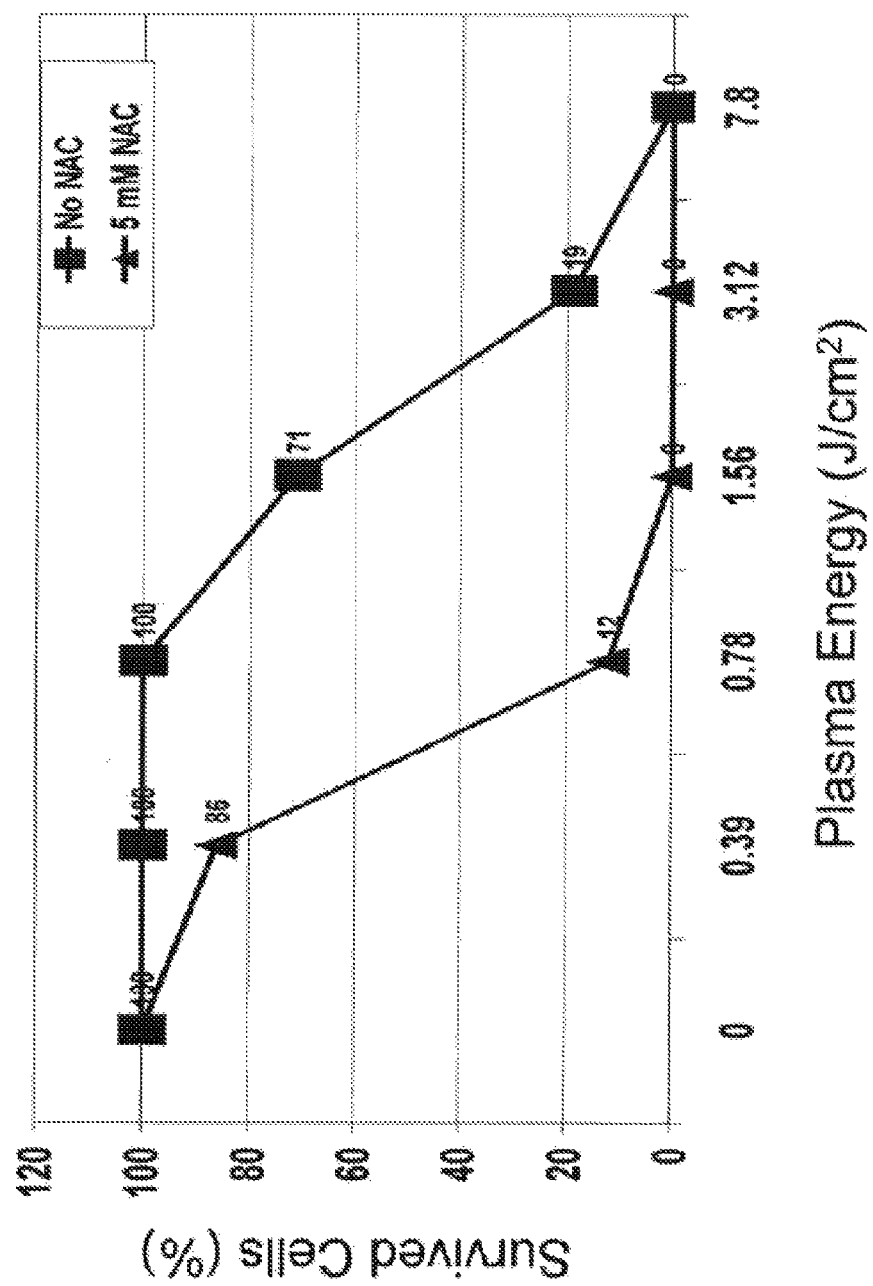
FIG. 8 shows the percentage of surviving *Escherichia coli* cells after being contacted with exemplary disinfection compositions comprising 5 mM NAC contacted with a plasma at varied energies compared to traditional direct plasma sterilization.
Figure 9:
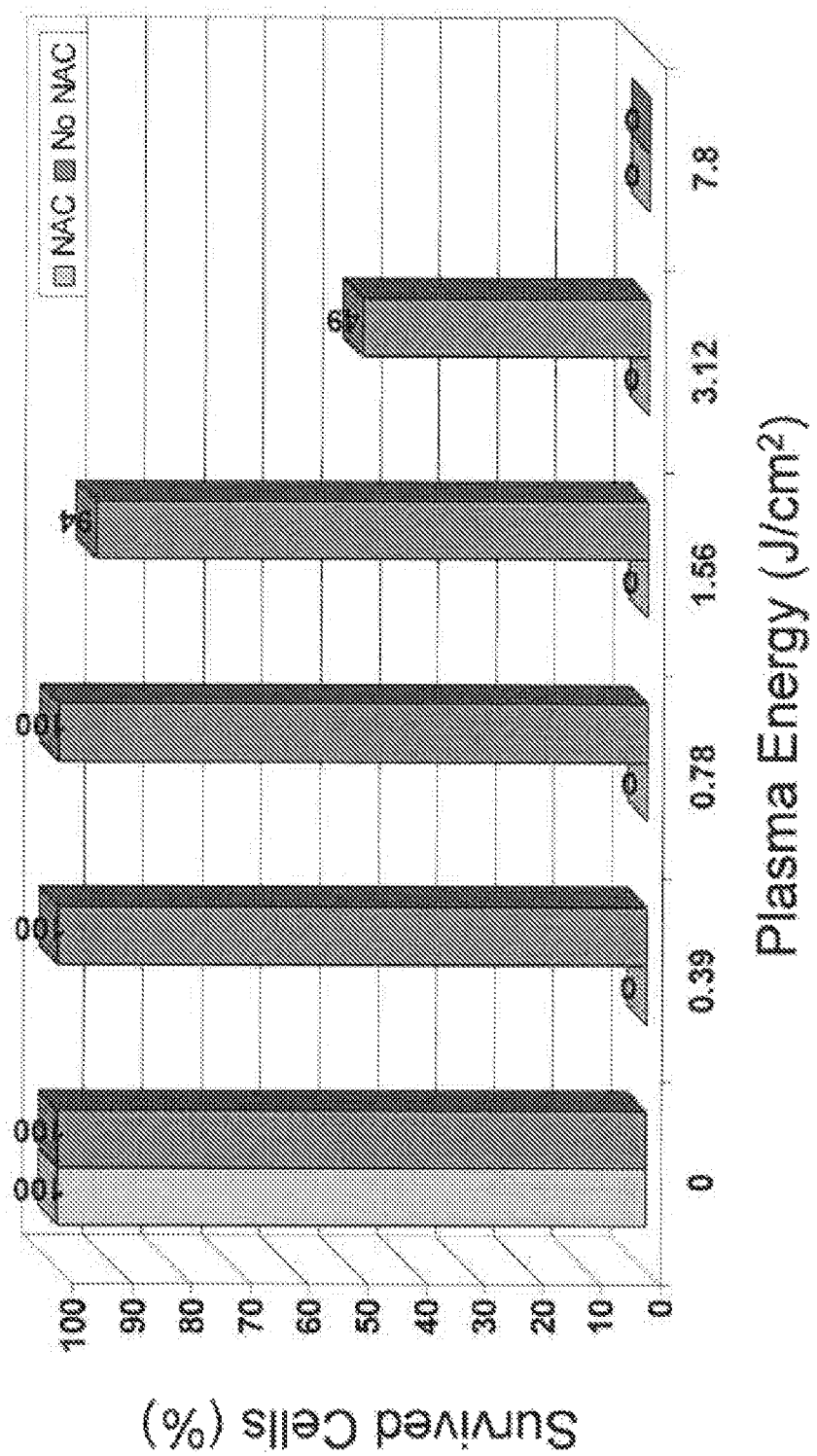
FIG. 9 shows the percentage of surviving *Escherichia coli* cells after being contacted with an exemplary disinfection composition comprising 5 mM NAC and phosphate buffered saline remotely contacted with plasma at different energies compared to traditional direct plasma sterilization.
Figure 10:
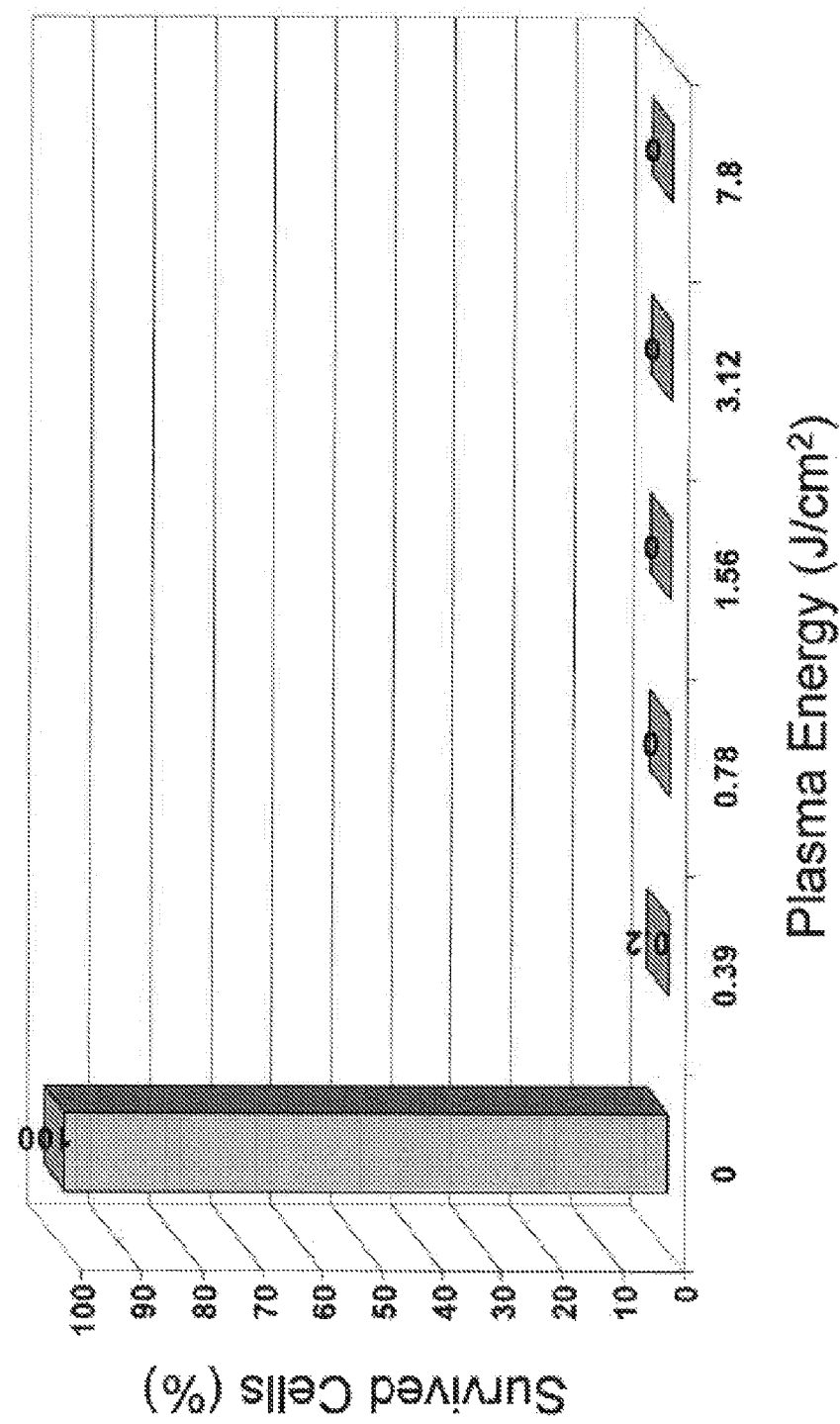
FIG. 10 shows the percentage of surviving *Escherichia coli* cells after being contacted with an exemplary disinfection composition comprising 5 mM NAC and phosphate buffered saline remotely contacted with plasma at different energies.
Figure 11:
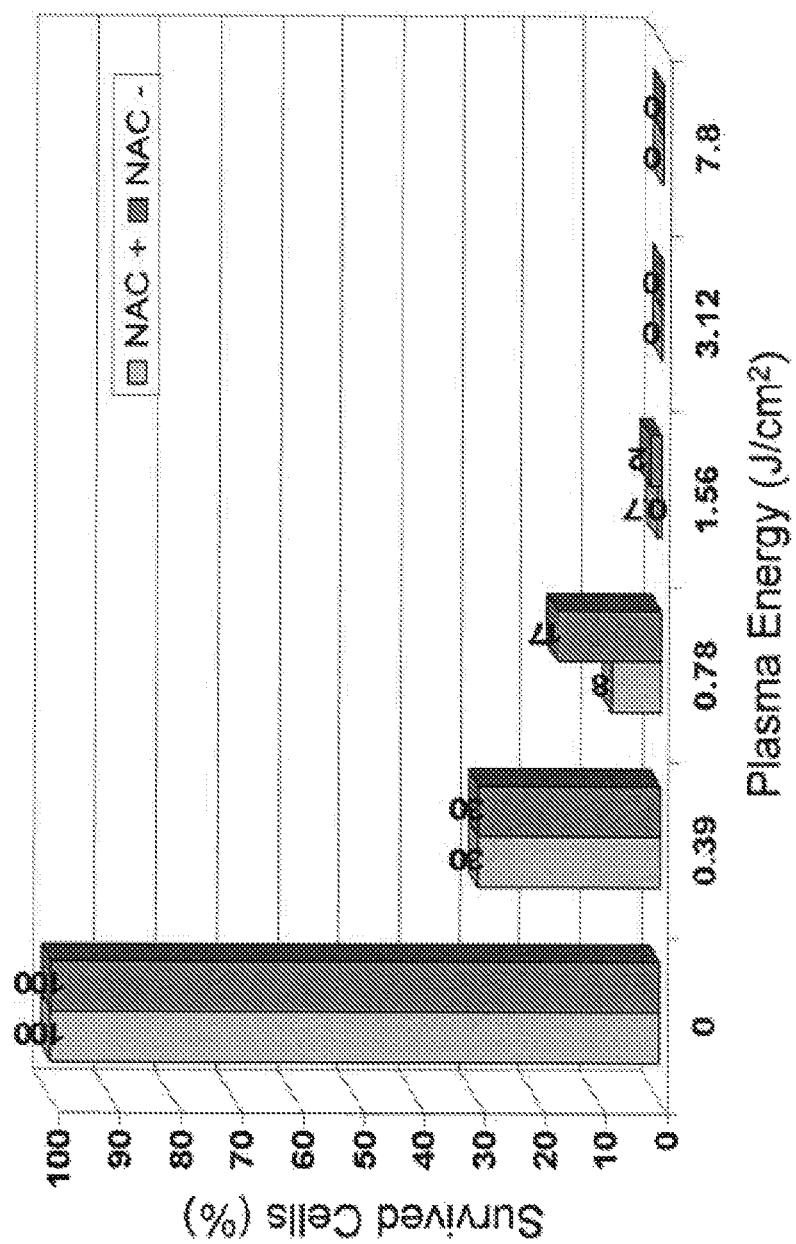
FIG. 11 shows the percentage of surviving *Escherichia coli* cells after initially being contacted with plasma, followed by being contacted with 5 mM NAC compared to traditional direct plasma sterilization.

FIG. 6 shows a comparison of cells treated with traditional direct plasma sterilization, NAC alone, and an exemplary disinfection composition comprising NAC contacted with a plasma. Disinfection is improved when the NAC is contacted with a plasma as compared to the treatments with plasma alone and NAC alone. This significant improvement is also shown in FIGS. 8 and 9 in which traditional direct plasma treatment is compared to treatment with an exemplary disinfection composition of the current subject matter. In additional embodiments, a surface may be first treated with a plasma and may subsequently be treated with an NAC composition as exemplified in FIG. 11.

The concentration of organic material may vary depending upon the surface being treated, the extent of disinfection required, and the type and amount of organic material in the disinfection composition. In certain embodiments, the concentration of organic material may be at least about 2.5 mM, at least about 5 mM, at least about 10 mM, at least about 30 mM, or at least about 50 mM.

In some embodiments, the disinfection composition may be generated and subsequently dried to produce a powder for later use. The powder may be distributed, reconstituted to sterilize or disinfect when applied in a manner similar to a disinfection composition recently created. See section titled Preparing and Reconstituting Dry Powder Disinfectants below. Certain embodiments provide for kits containing the powder to be reconstituted and instructions as to how to accomplish this reconstitution.

In still further embodiments, the disinfection compound may be or comprise water, alcohols (e.g., ethanol or isopropanol) or other appropriate liquid. The water may include or be free of added salts/buffering agents. Suitable aqueous liquids include saline, deionized water, tap water, and phosphate buffered saline (PBS), among others. Similarly, the alcohols may include any of the organic or additive materials described above, or be free from added additives or other materials. For example, disinfecting or sterilizing a surface may be performed by contacting liquid in the form of a mist with a non-thermal plasma formed in a gas to form a disinfection composition and contacting a surface with the disinfection composition, wherein the surface is at least partially disinfected upon contact with the disinfection composition. The liquid may be water or other appropriate liquid. The surface to be disinfected or sterilized may include, but is not limited to, steel, polyethylene, or polytetrafluoroethylene. The types of organisms that may be killed include, but are not limited to, *Escherichia coli, Staphylococcus aureus* (including methicillin-resistant *S. aureus*, MRSA), *Staphylococcus epidermidis, Acetinobacter*

*baumanii, Candida albicans*, and *Candida glabrata*, *P. aeruginosa*, and *K pneumonia*. In various embodiments, the plasma-treated water is applied to the pathogen as a mist, spray, or aerosol. Some sample mist flow rates range from 0.1 ml/min to 160 ml/min.

In certain embodiments, the disinfecting water or aqueous mixtures are prepared by exposing the water or aqueous mixtures to plasmas having energies of at least about 0.2 J/cm$^2$, at least about 0.4 J/cm$^2$, at least about 0.6 J/cm$^2$, at least about 0.8 J/cm$^2$, at least about 1 J/cm$^2$, at least about 1.5 J/cm$^2$, at least about 2 J/cm$^2$, at least about 3 J/cm$^2$, at least about 4 J/cm$^2$, at least about 5 J/cm$^2$, at least about 8 J/cm$^2$, at least about 10 J/cm$^2$, at least about 12 J/cm$^2$, at least about 14 J/cm$^2$, at least about 16 J/cm$^2$, at least about 18 J/cm$^2$, at least about 20 J/cm$^2$, or at least about 24 J/cm$^2$.

In certain embodiments, these disinfecting water or aqueous mixtures are capable of killing the pathogens described above, and including *Escherichia coli, Staphylococcus aureus, Staphylococcus epidermidis, Acetinobacter baumanii, Candida albicans*, and *Candida glabrata*. In other independent embodiments, these disinfecting water or aqueous mixtures are capable of at least partially (including completely) sterilizing surfaces (inactivating pathogens) described herein within 5 secs, 10 secs, 30 secs, 1 min, 3 min, 5 min, 10 min, and 30 minutes of contacting the plasma treated gels and the pathogens.

For example, and as described below (see Experiments Without Organic Materials Added—Series 3), free living planktonic forms of *E. coli, S. aureus* and MRSA, exposed to DBD plasma-treated phosphate buffered saline (PBS) were rapidly inactivated under clinically useful scenarios.

In some embodiments, the methods and systems described herein may be used to sterilize or disinfect biologics such as hands, arms, or face, and including at least one finger, palm, wrist, forearm, elbow, and/or upper arm. FIG. 27 is an exemplary device that may be used to disinfect (or sterilize) the arm or hand of a person. Shown is a disinfection or sterilization system having power supply 204 and disinfection station 202. Station 200 generates a non-thermal plasma using power supply 204 in the presence of one or more aerosols or mists of liquids, such as water or NAC. The plasma activates the one or more aerosols or mists of liquid, with the mist (or aerosol) being directed to disinfection area 208. A person places their hand 202 in the area 208 while station 200 is generating the plasma for disinfection or sterilization purposes. To further the ability to sterilize or disinfect, an additional solution, solution 206, may be added. Solution 206 may be the liquid aerosol or may be an additional liquid that provides for additional sterilization or disinfection capabilities.

Further embodiments provide devices for at least partially disinfecting a human body part, comprising a power supply for generating a plasma; a plasma-treating chamber in which a fluid and plasma can be introduced to form a disinfection composition; a disinfection chamber for contacting a human body part or medical device with the disinfection composition, wherein the human body part is at least partially disinfected upon contact with the disinfection composition.

The plasma may be generated by a dielectric barrier discharge, a corona discharge, or a pulsed corona discharge, ark, spark, gliding arc, radio frequency discharge, microwave discharge or any combination thereof and, in some cases, the plasma may be of different type applied at different times and in different locations.

The power supplies of such devices may generate non-thermal plasmas having an intensity of at least about 0.1 J/cm$^2$, or at least about 0.5 J/cm$^2$, or at least about 1 J/cm$^2$, or at least about 5 J/cm$^2$.

In certain embodiments, the devices may contain a means for aerosolizing or misting a liquid feed stream, such that the fluid takes the form of an aerosol or mist either before or while contacting the plasma. As with other embodiments described herein, the fluid may comprise water, saline, phosphate buffer composition, or a combination thereof. The water may be deionized or distilled or be obtained without treatment from clean commercial sources ("tap water"), and may contain or be free of added organic materials or additives. Various alcohols, preferably ethanol or isopropanol, may also be used in such devices.

The devices may use water or alcohol containing at least one added organic material as described herein, preferably comprising one or more amino acid, anti-oxidant, and/or an alginate gel, and preferably N-Acetyl Cysteine. The organic material may be partially or completely dissolved in the fluid. If present, separate embodiments provide that the organic material in the disinfection composition may be at a concentration of at least about 2.5 mM, at least about 5 mM, or at least about 10 mM.

As shown below, the devices may be used to disinfect medical devices (e.g., intravenous tubing, heplocks, intravenous catheters, a nebulizer, and urinary catheters) or human body parts (e.g., hand, arm, or portion thereof, including at least one finger, palm, wrist, forearm, or elbow).

Such devices may be configured such that the surface is contacted with the disinfection composition remote from the plasma. This can be accomplished, for example, by configuring the device such that the plasma-treating chamber is spatially separate from the disinfection chamber, and the two chambers are in fluid communication with one another. Alternatively, the plasma-treating chamber and the disinfection chamber may be the same chamber, and the device is configured to form the disinfection composition before allowing contact of the disinfection with the human body part or medical device (i.e., temporally separated).

Figure 28:
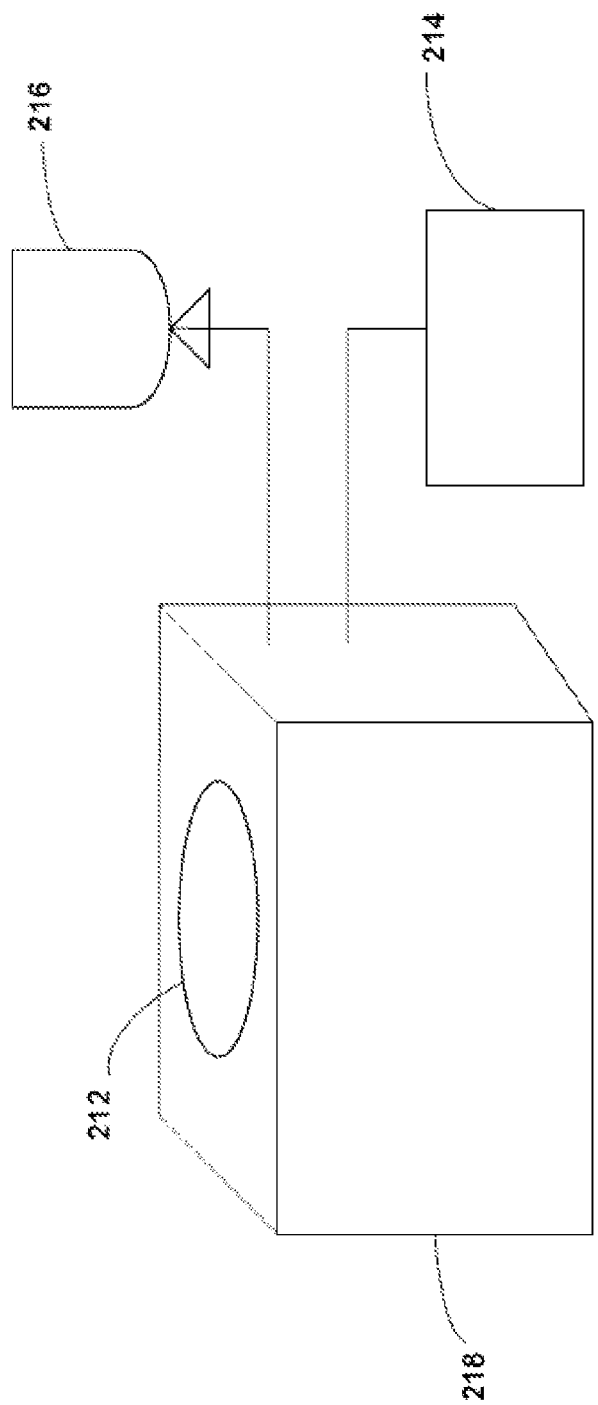
FIG. 28 is an alternate exemplary device that may be used to sterilize or disinfect the arm or hand of a person.

These concepts may be exemplified in FIGS. 27 and 28. That is, tools or other devices may be sterilized using a station similar to station 200 of FIG. 27. Referring to FIG. 28, station 218 is configured to sterilize or disinfect items placed into portal 212, which is similar to the disinfection area 202 of FIG. 27. As described with regards to station 200 of FIG. 27, station 218 uses power from power supply 214 to generate a non-thermal plasma in the presence of one or more aerosols or mists of liquids, such as water, alcohol, or NAC. The plasma activates the one or more aerosols or mists of liquid, with the mist (or aerosol) being directed to disinfection area 212. A device (not shown) is placed in area 212 while station 218 is generating the plasma for disinfection or sterilization purposes. To further the ability to sterilize or disinfect, an additional solution, solution 216, may be added. Solution 216 may be the liquid aerosol or may be an additional liquid that provides for additional sterilization or disinfection capabilities.

The present subject matter is further defined in the following Examples. It should be understood that these examples, while indicating preferred embodiments of the subject matter, are given by way of illustration only. From the above discussion and these examples, one skilled in the art can ascertain the essential characteristics of this subject matter, and without departing from the spirit and scope thereof, can make various changes and modifications of the subject matter to adapt it to various usages and conditions. Such modifications are considered to be within the scope of the present invention.

EXAMPLES

Experiments with Added Organic Materials—Series 1

Figure 12:
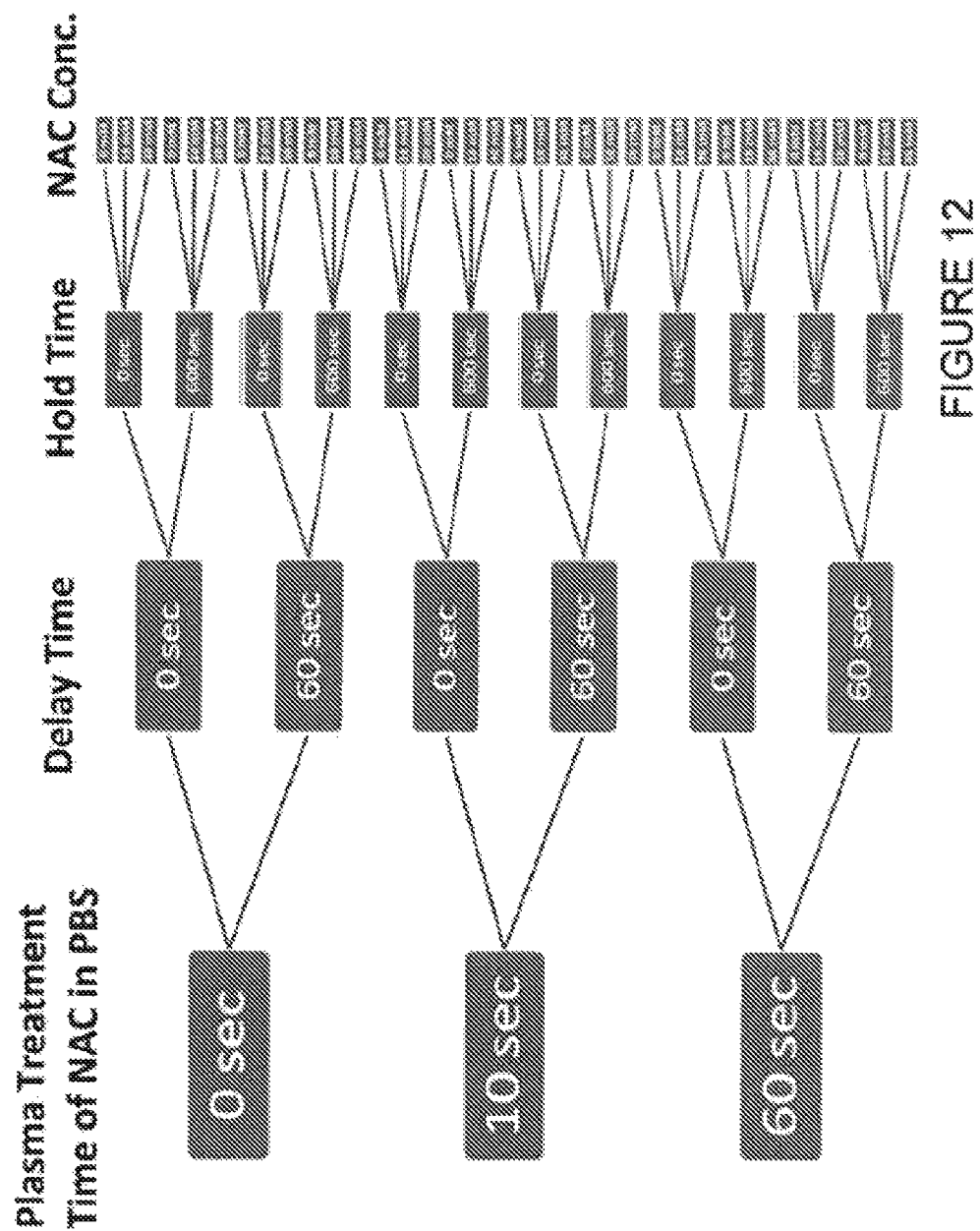
FIG. 12 is a schematic of experimental conditions for exemplary disinfection compositions.
Figure 13:
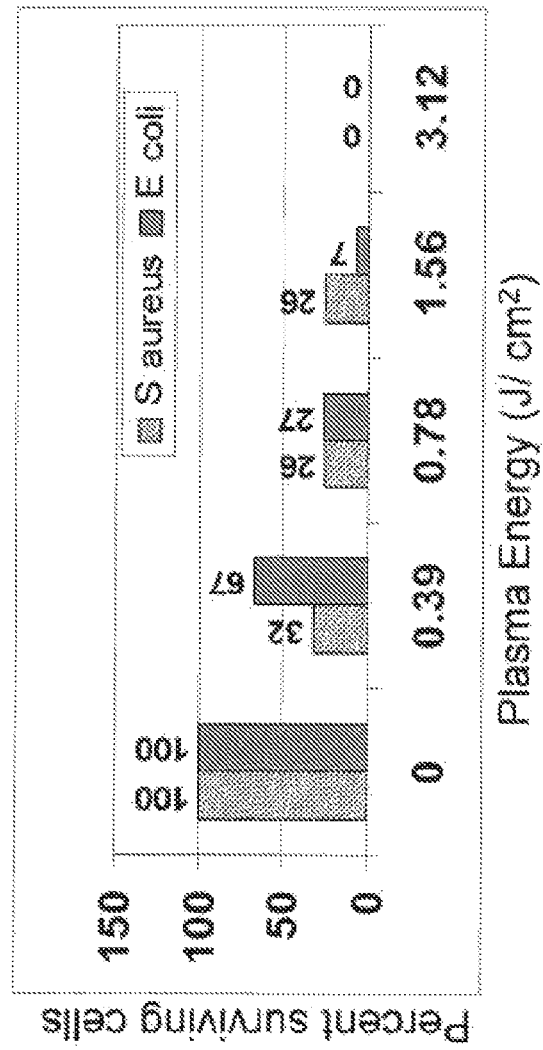
FIG. 13 shows a comparison of percentage of surviving cells of *S. aureus* and *E. coli* (7 log) allowed to dry on the surface of glass, immediately contacted with Plasma treated-NAC solution (5 mM) and mixed with no delay time, and holding time of 3 minutes.
Figure 14:
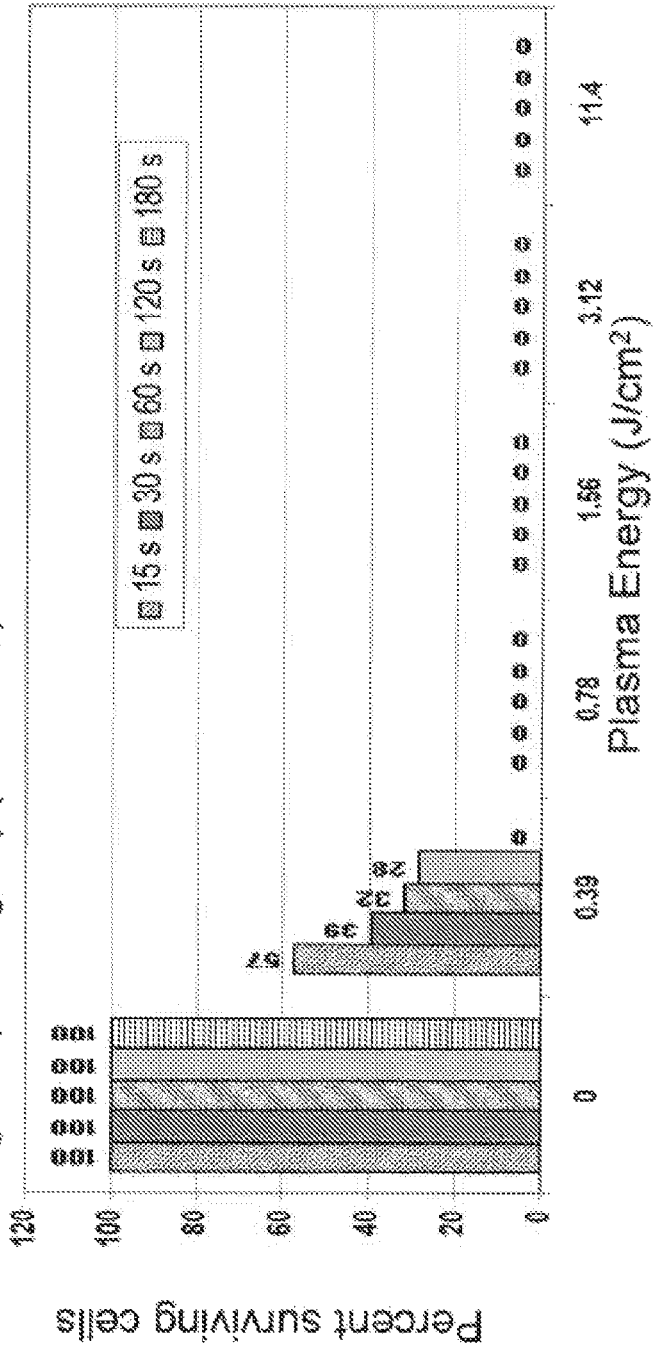
FIG. 14 shows the effect of holding time on cell survival percentage. A 5 mM NAC solution was treated with plasma over time, and applied almost immediately (no delay time) to *E. coli* suspension PBS (7 Log), and the mixture was held for variable time period before plated for colony counts.
Figure 15:
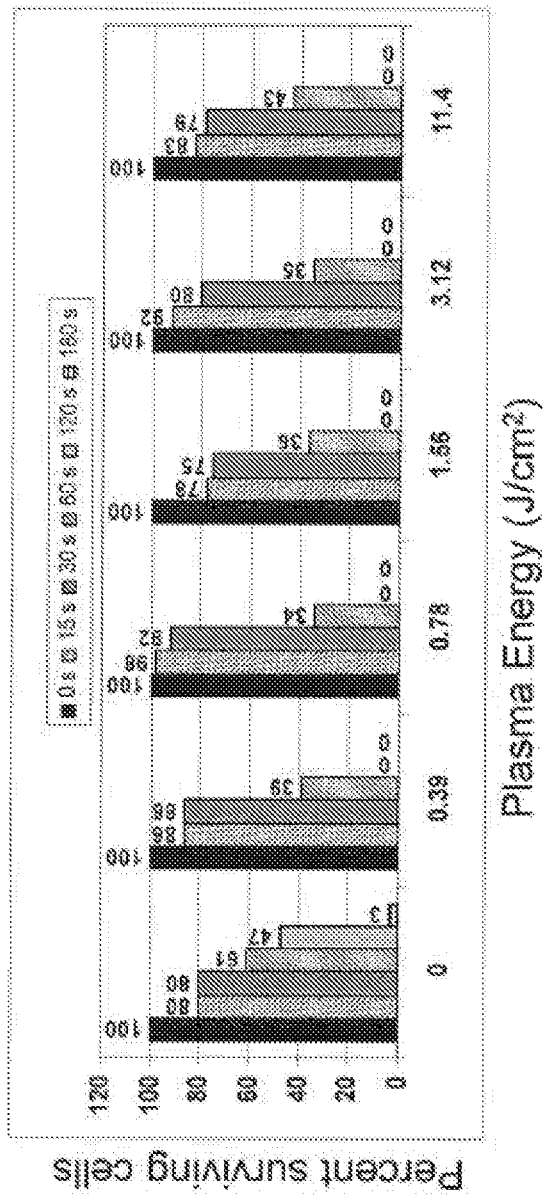
FIG. 15 shows the effect of holding time on cell survival percentage. A 5 mM NAC solution was treated with plasma over time, and applied almost immediately (no delay time) to *E. coli* suspension PBS (9 Log), and the mixture was held for variable time period before plated for colony counts.

FIG. 12 shows a schematic of experimental conditions for exemplary disinfection compositions for disinfection and sterilization of solutions comprising *Escherichia coli* cells. As used herein, "plasma treatment time" refers to the amount of time the organic material is contacted with the plasma to form a disinfection composition; "delay time" refers to the duration of time between formation of the disinfection composition and contacting a surface with the disinfection composition; and "hold time" refers to the amount of time the surface is contacted with the disinfection composition. The nomenclature for the following examples is as follows: plasma treatment time (seconds): delay time (seconds): hold time (seconds): NAC Concentration (mM). Thus, 0:0:0:0 stands for a plasma treatment time of 0 seconds, a delay time of 0 seconds, a hold time of 0 seconds, and a NAC concentration of 0 mM. Equal amounts of *Escherichia coli* cells were placed in Petri dishes (approximately 1,400 cells per dish) and were treated in duplicate per the parameters of FIG. 12. The plasma used for treatment of NAC was a DBD. Surviving *Escherichia coli* cells were visually observed and counted. If the number of surviving cells was too numerous to count these trials are indicated as "TNTC."

TABLE 3

Survival of Cells After Contact With Disinfection Composition With 60 Second Plasma Treatment Time

| Parameters | Trial A | Trial B |
| --- | --- | --- |
| 60:0:0:0 | TNTC | TNTC |
| 60:0:0:10 | TNTC | TNTC |
| 60:0:0:30 | 350 | 440 |
| 60:0:600:0 | TNTC | TNTC |
| 60:0:600:10 | 500 | 300 |
| 60:0:600:30 | 6 | 7 |
| 60:60:0:0 | TNTC | TNTC |
| 60:60:0:10 | TNTC | TNTC |
| 60:60:0:30 | TNTC | TNTC |
| 60:60:600:0 | TNTC | TNTC |
| 60:60:600:10 | 502 | 0 |
| 60:60:600:30 | 0 | 0 |

TABLE 4

Survival of Cells After Contact With Disinfection Composition With 10 Second Plasma Treatment Time

| Parameters | Trial A | Trial B |
| --- | --- | --- |
| 10:0:0:0 | TNTC | TNTC |
| 10:0:0:10 | TNTC | TNTC |
| 10:0:0:30 | TNTC | TNTC |
| 10:0:600:0 | TNTC | TNTC |
| 10:0:600:10 | TNTC | TNTC |
| 10:0:600:30 | 1 | 20 |
| 10:60:0:0 | TNTC | TNTC |
| 10:60:0:10 | TNTC | TNTC |
| 10:60:0:30 | TNTC | TNTC |
| 10:60:600:0 | TNTC | TNTC |
| 10:60:600:10 | TNTC | TNTC |
| 10:60:600:300 | 0 | 0 |

TABLE 5

Survival of Cells After Contact With Disinfection Composition With 0 Second Plasma Treatment Time

| Parameters | Trial A | Trial B |
| --- | --- | --- |
| 0:0:0:0 | TNTC | TNTC |
| 0:0:600:10 | TNTC | TNTC |
| 0:0:600:30 | TNTC | TNTC |

Sterilization increased with an increased plasma treatment time and increased concentration of NAC. Additionally, increased "hold time" had an impact on increased sterilization.

Experiments with Added Organic Materials—Series 2

Plasma Treatment of Liquids. The non-thermal plasma DBD plasma generator used in this work employed copper electrode (38 mm×64 mm) covered with a 1-mm glass slide (Fischer Scientific Inc., Pittsburgh, Pa.); a 2 mm fixed discharge gap; and a customized liquid container was designed to maintain a liquid column of 1 mm. De-ionized water (DIW) (MP Biomedicals Inc., Solon, Ohio), PBS, or N-acetyl-cysteine (NAC) (Sigma Chemical Co., St. Louis, Mo.) was treated separately at different time points. A stock solution of NAC (100 mM) was prepared in 1× sterile PBS and sterilized through a filter; aliquots were stored at −20° C. until used. A freshly prepared working solution of 5 mM NAC in PBS was used for subsequent experiments. All liquids were treated for 0, 1, 2, and 3 min under these conditions.

Culture and Isolates of Bacterial Pathogens. *Escherichia coli* (ATCC25922), *Staphylococcus aureus* (ATCC25923), *Acinetobacter baumannii* (ATCC19606), and *Staphylococcus epidermidis* (ATCC12228) strains were purchased from American Type Culture Collection (ATCC, Manassas, Va.). All strains were maintained and used as overnight cultures in trypticase soy broth (TSB) for primary inoculations according to the supplier's guidelines. Reference strains of *Candida albicans* and *Candida glabrata* (obtained from Dr. Thomas Edlind, Drexel University College of Medicine) were grown in yeast extract-peptone-dextrose (YPD) medium. Hydrogen peroxide (Sigma) or 70% ethyl alcohol was used as the known biocide agent and either TSB alone or PBS alone was used as the negative control, as appropriate.

Plasma Fluid-Mediated Bactericidal and Fungicidal Activity. A given pathogen was cultured overnight, inoculated (10 μl) into TSB medium (10 ml), and incubated at 37° C. for 4 hours on an orbital shaker incubator; the optical density at 600 nm ($OD_{600}$) was adjusted to 0.2 before use. The culture dilution thus prepared (1:100) was mixed with plasma-treated liquids (50 μl:50 μl) and held together at room temperature for 0- to 15-min intervals. After holding (holding time), the culture was diluted appropriately with sterile 1×PBS and spread on trypticase soy agar plates to incubate at 37° C. for 24 hours. After the culture was incubated, the colony forming units (CFU) were counted to quantify surviving pathogen cells. Some of the experiments were carried out using $10^6$ to $10^9$ CFU/ml (as initial cell numbers) to determine cell density-dependent rates of inactivation. Plates that did not show any growth were incubated further up to 72 h and observed every 24 h for possible growth. Similarly, the cultures of 0.2 $OD_{600}$ were diluted (1:100) and exposed to plasma-treated fluid (50 μl:50 μl), mixed, and held for variable times. The sample was centrifuged at 8000 rpm for 10 min; the supernatant was removed to collect the cell pellet. The pellet was re-suspended in XTT reagent to carry out the XTT assay The untreated or treated biofilms were processed for XTT assay to determine whether the bacteria embedded in the biofilms had been inactivated. Ethanol (70%) was used as a positive control for the biofilm experiments.

Delay Time, Holding Time, and Fluid-Aging Experiments.

Holding time (also known as contact time) was defined as the time that plasma-treated liquid came in contact with the bacterial suspension. To evaluate the effect of holding time, plasma-treated fluid was exposed to bacteria for variable periods of time. For 0 min holding time, plasma-treated fluid was exposed to bacteria and then immediately mixed thoroughly by micropipetting; a standard colony-counting assay was performed. For longer holding times, the plasma-treated fluid and bacteria were mixed and held together for the desired time in the same tube at room temperature after the desired time, the standard colony-counting assay was performed.

Delay time is defined as the time that starts immediately after treatment with plasma until the exposure of the plasma-treated liquid to bacteria. To evaluate the effect of delay time, different time points were selected (0 min-3 mo). For 0 min delay time, plasma-treated liquid was exposed to bacteria immediately after plasma treatment, and the standard colony-counting assay was performed. For prolonged delay time points, plasma-treated liquid was stored either at +4° C. (in the refrigerator) or at room temperature in microtubes sealed with parafilm. Once the tube containing the sample was opened, to avoid contamination of the fluid, the sample was used for the experiments at hand and never reused.

For aging experiments, the plasma-treated NAC solution was kept in a thermostatically controlled incubator set to an elevated temperature (55° C.) and incubated over time. The protocol of the U.S. Food and Drug Administration (FDA) was used for aging pharmaceutical compounds. In brief, 1 ml of plasma-treated NAC solution was immediately transferred into 3-ml glass vials; the screw caps were replaced; the vials were sealed with parafilm and put upright in racks kept in the incubator. At the indicated time point, one vial was removed, and the antimicrobial property of the liquid was tested using the colony count assay described above.

Data Analysis. All experiments had built-in negative and positive controls as stated. The initial concentrations of bacteria (untreated samples or 0 time treatment samples) were taken as 100% surviving cells to calculate percent inactivation (unless specifically stated Wherever needed, Prism software v4.03 for Windows (Graphpad, San Diego, Calif.) was used for analysis. A P value was derived using pair comparisons between two bacterial groups with a student t test and one-way analysis of variance for multiple comparisons. A P value of <0.05 was considered statistically significant.

Figure 16:
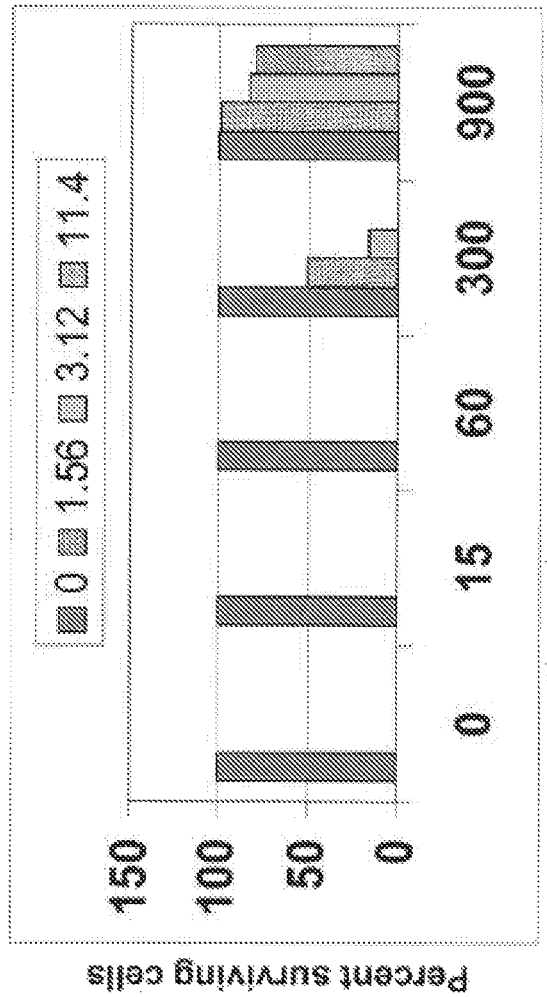
FIG. 16 shows the effect of delay time on cell survival; NAC (5 mM final) in PBS treated with Plasma over the time, and was kept a side (delayed mixing with bacteria) for variable times (Delay Times) before mixing with *E. coli* (7 log) cultures. The mixture was held for 1 min (Holding Time) before transfer for colony assay. Bar represents the amount of plasma energy (c/cm$^2$) applied to NAC solution.
Figure 16A:
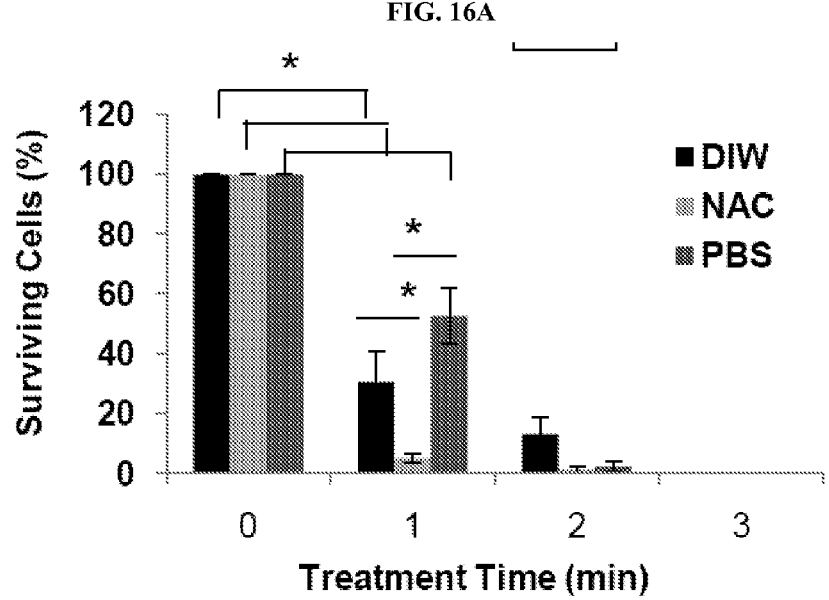
FIG. 16A shows the data associated with Experiments With Added Organic Materials—Series 2, below, showing that fluid-mediated plasma inactivates *E. coli* (1×10$^7$ CFU/ml) (sterilizes) in a time-dependent manner. Plasma-treated NAC solution has stronger antimicrobial properties and a significantly greater biocidal effect than treated de-ionized water (DIW) or phosphate-buffered saline (PBS).
Figure 16B:
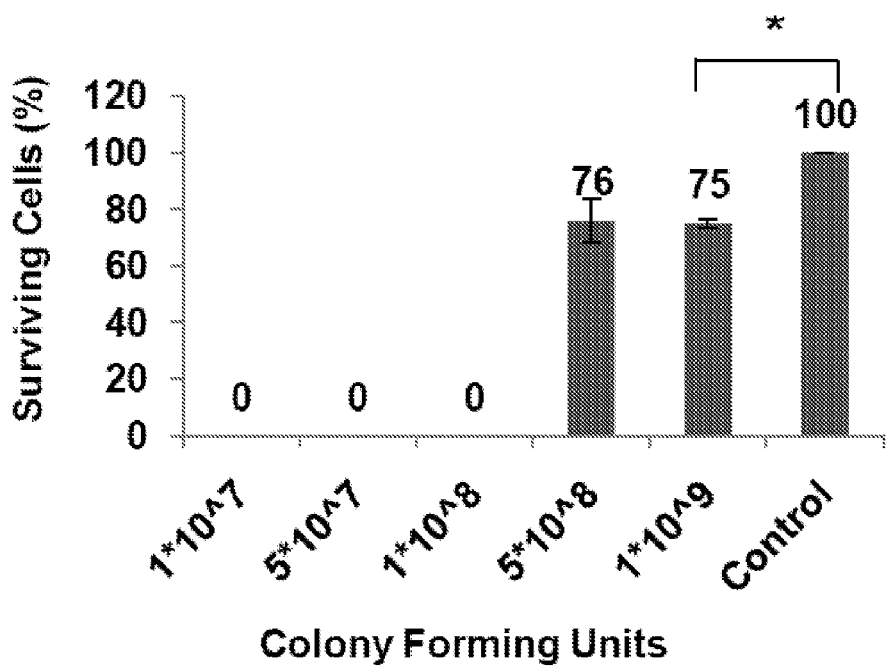
FIG. 16B shows that treated NAC solution causes cell density-dependent inactivation of *E. coli*. Within 3 min holding (contact) time, it inactivated up to 1×10$^8$ CFU/ml. (*, P value <0.05, against comparable conditions). See Experiments With Added Organic Materials—Series 2, below.

Results: Plasma-Treated Liquids Inactivated Bacteria in a Concentration-Dependent Manner. FIG. 16A shows that all three plasma-treated liquids (NAC solution, PBS, and de-ionized water) carry strong antimicrobial properties; and less than 3 min of treatment with plasma generated a sufficient amount of energy transfer into the liquids to effect complete inactivation of planktonic $E.\ coli$. Even by the end of 2 min, there was significant inactivation by the NAC solution (P<0.05), PBS (P<0.05), or de-ionized water (P<0.05) compared with the respective controls (0 min or no treatment). The plasma-treated NAC solution had the most powerful antimicrobial effect. With the treatment for 1 min (14.5 J/cm$^2$), it inactivated a highly significant amount of $E.\ coli$ (P<0.05) compared to de-ionized water or PBS alone for comparable times. During exposure to plasma-treated liquid, free-floating planktonic bacteria ($10^7$ CFU/ml) were found to be inactivated. Therefore, cell suspensions of various CFUs of $E.\ coli$ were exposed to plasma-treated liquids. FIG. 16B shows colony assays that indicate rapid inactivation of bacterial cells. The CFUs of the initial cell suspensions were considered to be 100%, and the rates of inactivation were compared. The treated liquid has shown 100% inactivation (sterilization) when exposed to ~$1 \times 10^8$ CFU/ml and ~25% inactivation with $5 \times 10^8$ to $1 \times 10^9$ CFU; it exhibits strong antimicrobial effects (P<0.05) compared with the respective untreated samples.

Figures 1, 16C:
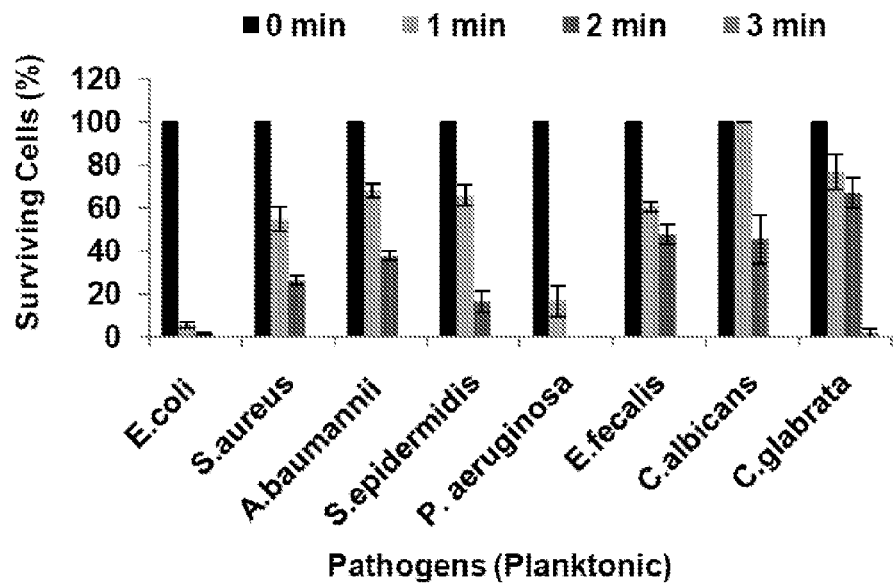
FIG. 16C shows data that plasma-treated antimicrobial NAC solution inactivates a wide array of pathogens both in planktonic form (C-1) and biofilm-embedded form (C-2). Three minutes of plasma treatment produced sufficient antimicrobial properties in solution, inactivating almost all pathogens in their planktonic and biofilm forms, except *C. albicans* and *C. glabrata* (which required 3.2 min; data not shown). (Non-treated [0 min] samples were considered 100%). See Experiments With Added Organic Materials—Series 2, below.
Figures 2, 16C:
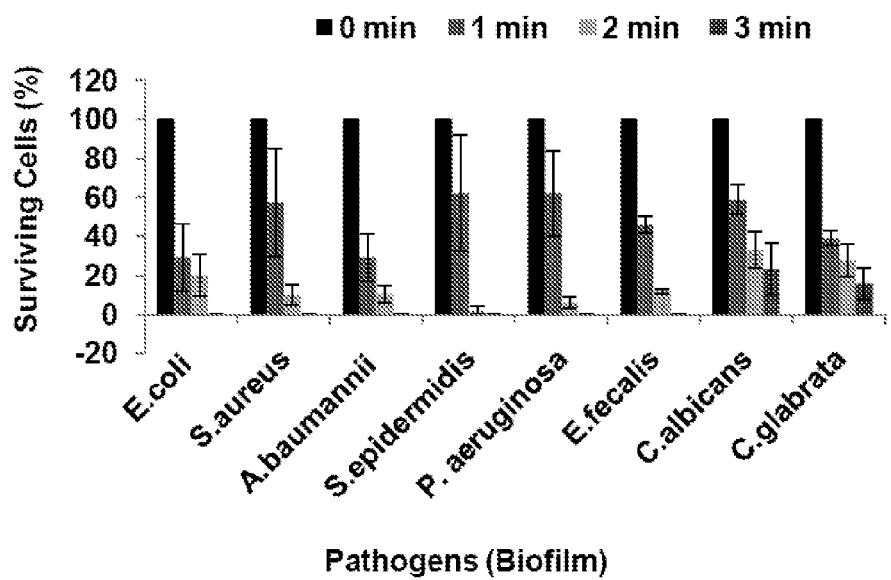

Plasma-Treated NAC Solution is a Powerful Antimicrobial Agent Against a Range of Pathogens. A range of common pathogens, such as $S.\ aureus,\ S.\ epidermidis,\ A.\ baumannii,\ C.\ albicans$, and $C.\ glabrata$, in addition to $E.\ coli$, were tested at concentrations of NAC (1 mM-20 mM) with or without plasma treatment. It was found that 5 mM was sufficient and showed a linear relationship during inactivation studies in colony assays. Higher concentrations of NAC did not show significantly different efficacy (data not shown). Studies in planktonic forms showed that the NAC solution completely inactivated all of the pathogens tested (FIG. 16C-1 & C-2) after 3 min of treatment with plasma. Only $C.\ glabrata$ required 3.2 min (195 sec) of treatment with the liquid to achieve 100% inactivation (sterilization) of this fungal pathogen (data not shown). Most of the pathogens in their biofilm form were equally or slightly more sensitive to the biocidal effect of the treated NAC solution.

Figure 16D:
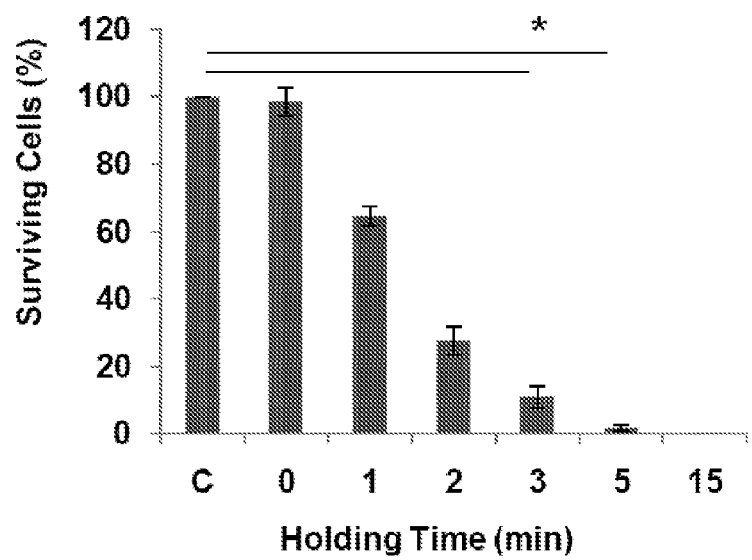
FIG. 16D shows the holding (contact) time required by plasma-treated NAC solution to complete inactivation of *E. coli* bacteria. The graph shows a significant, rapid decline in surviving *E. coli* as holding time increases. (*, P<0.05; against control, C).
Figure 16E:
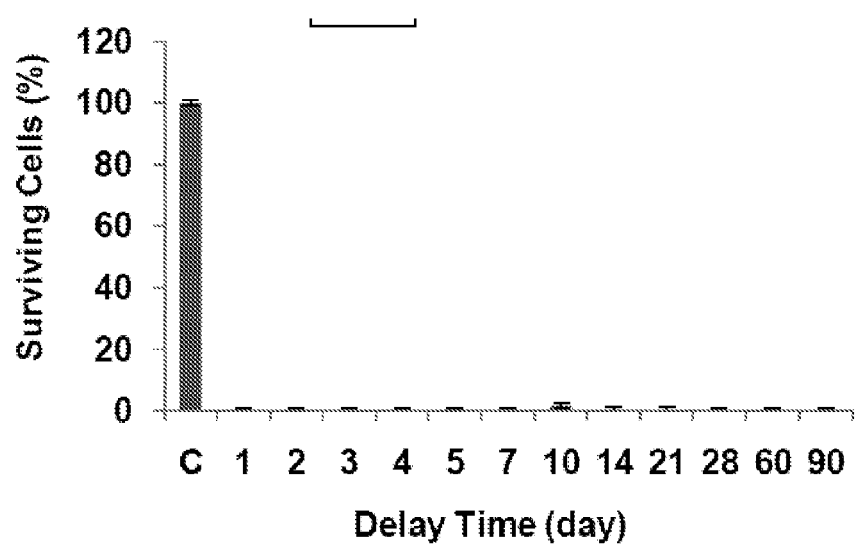
FIG. 16E shows that plasma-treated NAC solution retains antimicrobial effects up to 90 days at room temperature. See Experiments With Added Organic Materials—Series 2, below.

Determination of Holding Time, Delay Time, and Accelerated Aging of Solution. The contact time (holding time) of the antimicrobial agent with the pathogen is critical. Often, the biocidal effect is proportional to the initial contact time. FIG. 16D shows that, on exposure to the plasma-treated NAC solution, significant inactivation of $E.\ coli$ occurred from 2 min of holding time onward (P values for 2, 3, and 5 min against 0 min <0.05); after about 5 min, the bacteria were ~98% inactivated; after less than 15 min, the bacteria were completely inactivated (sterilized), upon. Similarly, to determine how long plasma-treated fluids retain antimicrobial effect at room temperature, delay time experiments were done. That is, mixing the post-treatment fluid (NAC solution) with the pathogen was delayed to determine whether the fluid lost its antimicrobial properties. FIG. 16E shows the antimicrobial efficacies of treated liquid delayed over time, post-treatment. It is apparent that treated fluid retained significant antibacterial effect (P<0.05; against control, C) for up to 90 days and showed complete inactivation of $E.\ coli$.

Figure 16F:
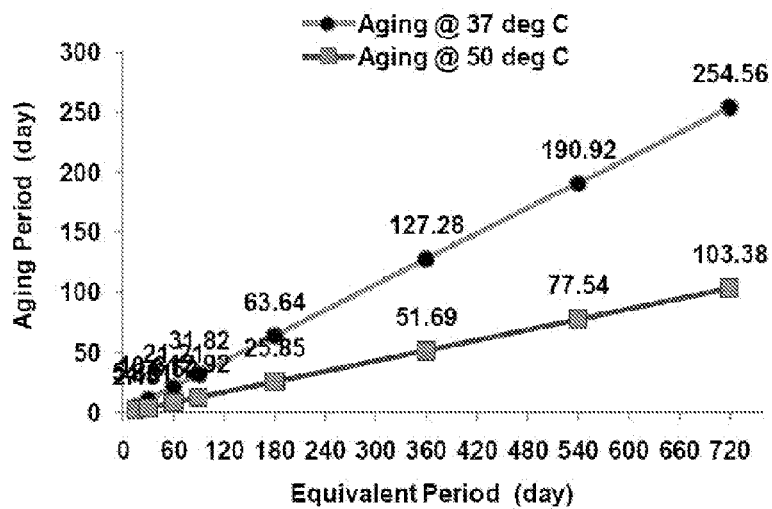
FIG. 16F shows accelerated aging (maturation) data of treated NAC solution at elevated temperature of 50° C., demonstrating that for ~2 years of equivalent time, the treated solution retains strong biocidal activity, a quality required by an ideal antimicrobial solution. See Experiments With Added Organic Materials—Series 2, below.
Figure 16G:
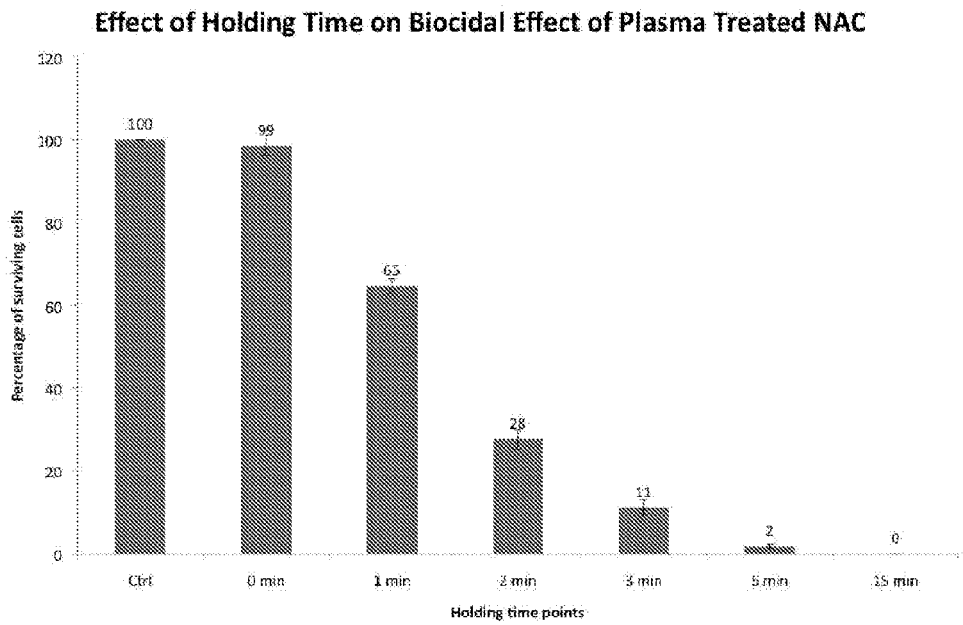
FIG. 16G shows the effects of hold time on biocidal effect, on exposure of plasma-treated NAC on *E. coli*. For 0 minute hold, bacteria were exposed to treated NAC, then immediately plated. The other times indicate hold times prior to plating.

Experiments were also conducted to assess the shelf life of the plasma-generated antimicrobial properties of the NAC solution, using accelerated aging scenarios for medically important solutions and devices at 37° C. and 50° C. over time, equivalent to 2 years of delay time at room temperature. FIG. 16F illustrates days of accelerated aging time at the respective temperatures and equivalent delay time at room temperature. Complete inactivation (sterilization) was observed when $E.\ coli$ at 107 CFU/ml were exposed to the solution. Because there were no colonies, the data are not shown. This result indicates that the plasma-treated NAC solution has the potential to act as an antimicrobial solution for local application.

Experiments with Alginate Gels—Series 1

Freshly prepared calcium alginate gels were directly treated with plasma (0.6 W/cm2; 1250 Hz) over time at room air, and pathogen was inoculated onto the alginate dressing. After a contact time of 15 minutes, the pathogen cells were harvested and tested for viability. Standard colony and XTT assays were used to evaluate biocidal efficacies. Scanning electron microscopy (SEM) was used to identify any gel surface-associated changes. *Staphylococcus aureus, S. epidermidis, Acinetobacter baumannii, Escherichia coli, Candida albicans*, and *C. glabrate* were tested as representative pathogens ($10^6$-$10^9$ CFU/mL). The thickness of the dressing was 1 mm and the distance between plasma probe and the gel surface was kept 1 mm constant.

The results showed that plasma treatment of alginate gels generated a strong biocidal property by completely inactivating (sterilizing) all of the pathogens tested within 15 seconds of plasma treatment. Optimization experiments revealed that 15 minute contact time was sufficient for complete inactivation of the pathogens even at $10^8$ CFU/mL. In 1 min of plasma treatment and 15 minutes of contact time, $10^9$ CFU/mL were completely inactivated. The biocidal effect was retained in the dressing for more than a month at room temperature. SEM imaging revealed no damage of the gel surfaces even upon plasma treatment of 3 minutes.

Experiments with Alginate Gels—Series 2

Dressing Preparation—Sodium alginate (M/G Ratio 1.6, Sigma-Aldrich, USA) was suspended in deionized $H_2O$, sterile filtered, poured into a mold, and then cross-linked with calcium to form circular hydrogels (26 mm diameter). Hydrogels were then treated with non-thermal, dielectric barrier discharge, micropulse plasma (1.2 Watt/cm$^2$, 31 kV, 1500 Hz) for three minutes. The plasma was generated using an electrode constructed with a 38×64 mm copper plate insulated in silicone and a 1 mm-thick glass sheet. The discharge gap between the bottom of the quartz and the treated sample surface was fixed 1 mm for treatment. Silver-(Acticoat® Smith & Nephew, a dressing made from alginate fibers coated in silver nanoparticles) and chlorhexidine-containing (Tegaderm CHG®3M, a dressing made from sodium alginate with chlorhexidine in suspension) dressings were used for comparison to the test dressings. Sontara (DuPont) a sterile, nonwoven absorbent material was used as a control. 26 mm discs were prepared in an aseptic manner and kept in sterile vials for use in the log reduction assays.

Log Reduction Assay—Untreated alginate hydrogel and Sontara were used as controls. For aerobic bacteria, colonies from an overnight culture were inoculated in 5 mL of tryptic soy broth and incubated for 4 to 6 hours at 37° C. to reach an ODU 600 of 0.2 (0.5 McFarland turbidity). Volumes of 50 μl of the test bacterial suspensions were transferred onto the dressings in sterile vials. After 15 minutes of incubation at room temperature, samples were washed for 5 minutes with 10 mL sterile PBS with gentle agitation to homogenize the solution, out of which triplicate samples were taken. Bacterial survival numbers were obtained using a standard plate count procedure, and the log reduction was calculated as the difference between the log numbers of bacteria surviving on the control dressings and the test dressings. Plates remained incubated 72 hours to assess for delayed reactivation.

SEM Observations—The morphologies of alginate hydrogels before and after exposure to non-thermal plasma and of bacteria on the surface of those hydrogels were observed using the Zeiss Supra 50VP Scanning Electron Microscope. Samples were fixed, dehydrated, and sputter-coated with a platinum/palladium alloy prior to imaging.

Figure 17:
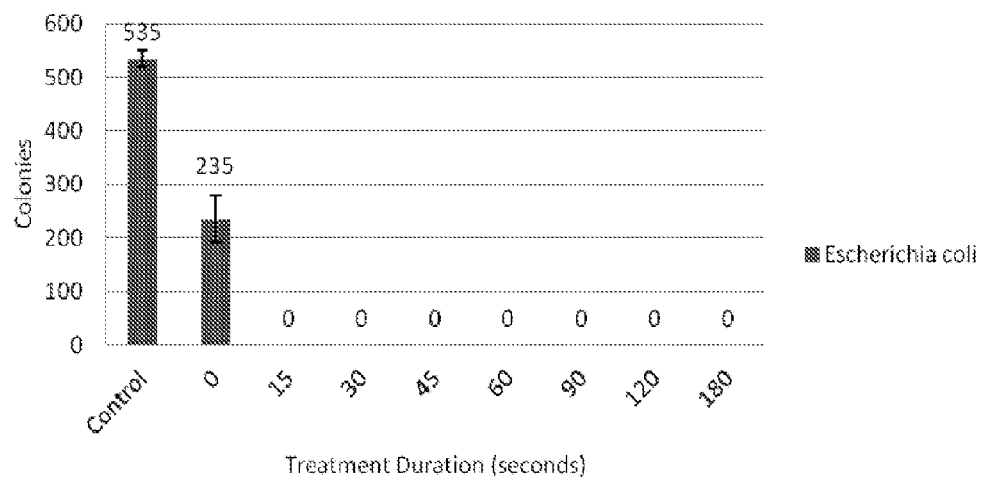
FIG. 17 shows complete inhibition of 10$^7$ CFU/mL *E. coli* by alginate gels exposed to 15 seconds of plasma treatment (see Experiments with Alginate Gels—Series 2 below). Note that the treatment duration is the time the alginate gels were subjected to plasma before inoculation with the *E. Coli*.

Results—Gels exposed to as few as 15 seconds of non-thermal plasma treatment resulted in complete inactivation of $10^7$ CFU/mL *E. coli* (control material yielded only a 2.7-log reduction and untreated alginate gels yielded a 2.3 log-reduction). The bactericidal effect was also complete with longer durations of plasma treatment (FIG. 17). Comparison of SEM images suggests that exposure to non-thermal plasma does not alter the hydrogel surface (image 1). SEM micrographs of bacteria on the surface of treated hydrogels show extensive damage as compared to those on an untreated hydrogel (not shown).

Figure 18:
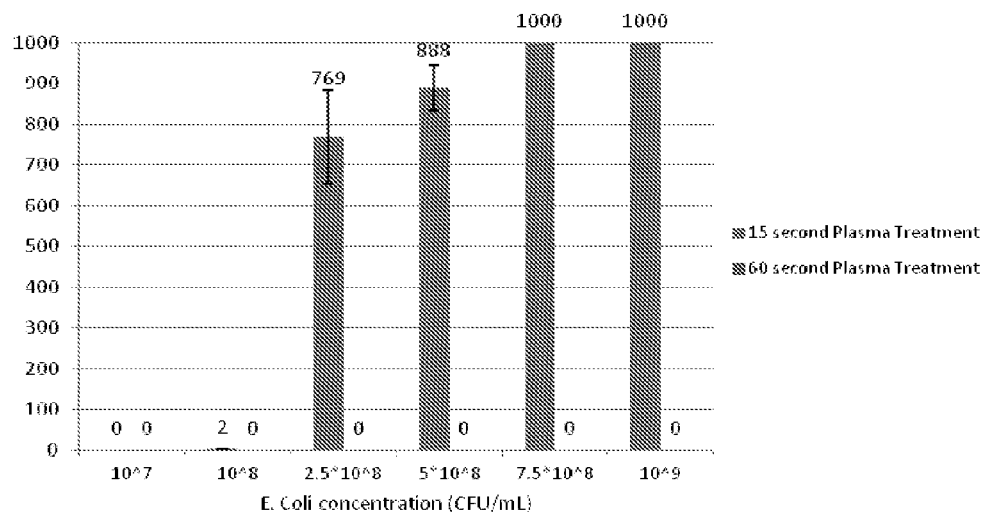
FIG. 18 shows complete inhibition of 10$^9$ CFU/mL *E. coli* by alginate gels exposed to 60 seconds of plasma treatment (see Experiments with Alginate Gels—Series 2 below). Note that data for 15 second (left) and 60 second (right) treatments are presented for each *E. Coli* concentration.

In order to determine the killing capacity of the plasma-treated gel dressings, increasing concentrations of bacteria were exposed to gels treated with either 15 seconds or 3 minutes of plasma exposure. As illustrated in FIG. 18, gels treated with 3 minutes of gel exposure completely inactivated $10^9$ CFU/mL *E. coli*, while gels treated for 15 seconds were able to completely inactivate $10^8$ CFU/mL *E. coli*, but any greater concentration exceeded the bactericidal capacity.

Figure 19:
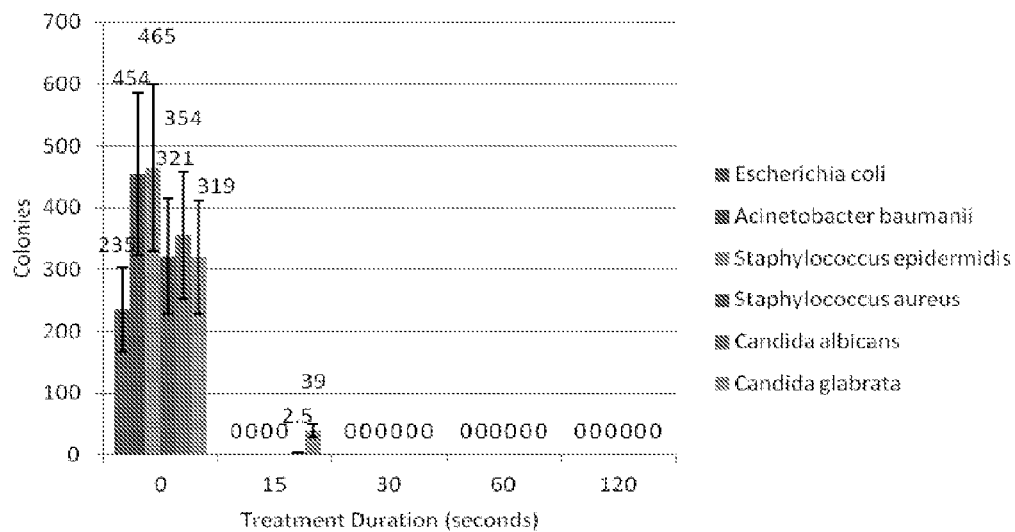
FIG. 19 shows complete inhibition of 10$^7$ CFU/mL of various pathogens by gels exposed to 15 seconds of plasma treatment (see Experiments with Alginate Gels—Series 2 below). Note that the data for each bacteria strain is presented for each treatment duration (top to bottom corresponds to left to right; e.g., data for *E. Coli* is leftmost and for *Candida glabrata* is rightmost within each treatment duration).

In order to test the spectrum of activity, a variety of pathogens were exposed to the plasma-treated gel dressings. Pathogens tested were: *Escherichia coli* ATCC 25922, *Staphylococcus aureus* ATCC 25923, *Staphylococcus epidermidis* ATCC 12228, *Acetinobacter baumanii* ATCC 19606, *Candida albicans*, and *Candida glabrata* (Candida specimens generously provided by Dr. Thomas Edlind, PhD, Drexel University College of Medicine). As demonstrated in FIG. 19, the gels treated with 15 seconds or longer of plasma exposure resulted in complete inactivation of all pathogens at $10^{7th}$ concentration.

Figure 20:
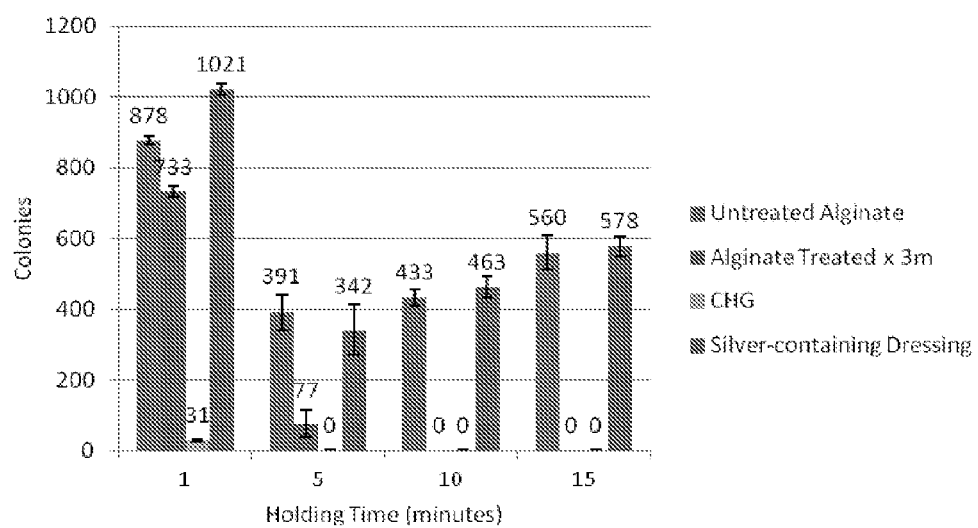
FIG. 20 shows the results of alginate gels exposed to 3 minutes of plasma treatment result in total inhibition of 10$^7$ CFU/mL *E. coli* after 10 minutes of contact (see Experiments with Alginate Gels—Series 2 below). Note that the data for treatment is presented for hold time (i.e., top to bottom of legend corresponds to left to right within each hold time.

Speed of killing was examined by carrying out the log-reduction test while varying the duration of contact between the test dressing and bacteria (the holding time). The plasma-treated gel dressings (3 minutes of plasma treatment pre exposure) were compared to the commercially available chlorhexidine and silver based dressings listed above. The chlorhexidine dressing resulted in the most rapid killing with a 1.5-log reduction at 1 minute and complete inactivation at 5 minutes (FIG. 20). The plasma-treated gels resulted in total inactivation at 10 minutes. The performance of the silver containing dressing and the untreated alginate were roughly equivalent over the 15-minute time period examined.

Figure 21:
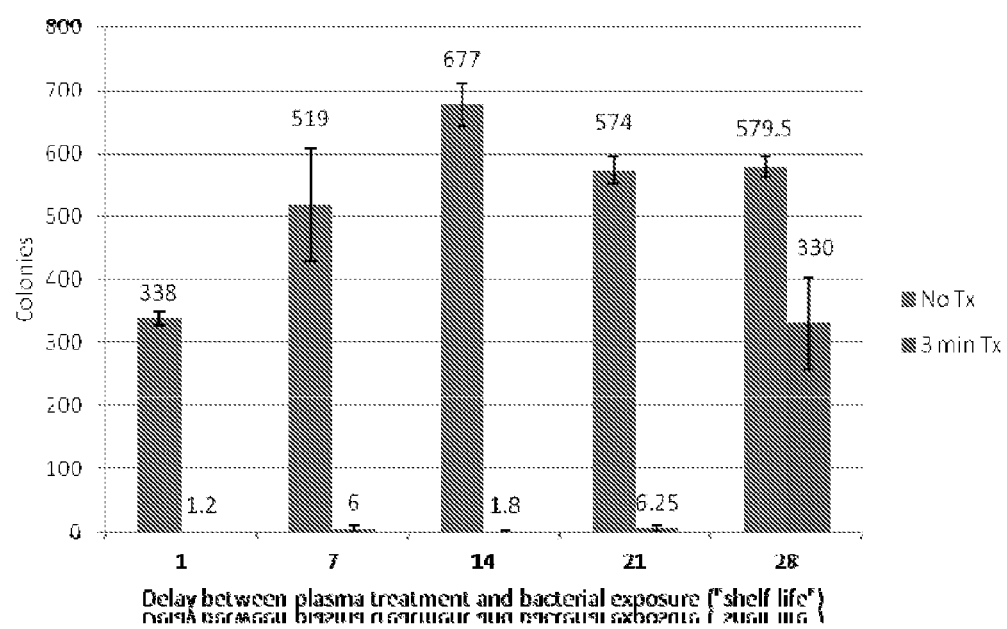
FIG. 21 shows that the effect of gels exposed to 3 minutes of plasma treatment lasts 3 weeks (see Experiments with Alginate Gels—Series 2 below). Note that Tx refers to calcium alginate gels treated with non-thermal non-equilibrium dielectric-barrier discharge plasma (power density, 0.29 W/cm$^2$), and delays are given in days (1, 7, 14, 21, and 28). For each day delay, data for No Tx is on left and 3 min Tx is on right.

The antimicrobial effect of the plasma-treated gel dressings started to dissipate by four weeks of storage (FIG. 21). After treatment, the gels were stored in either a non-airtight container (where the treated surface did not come in contact with anything but air) placed in a refrigerator and kept at constant temperature and humidity or in a vacuum-sealed container (where the treated surface came in contact with the plastic container). Regardless of storage method, the gels maintained the antimicrobial effect for 21 days but it was diminished by 28 days.

Experiments without Organic Materials Added—Series 1

Figure 22:
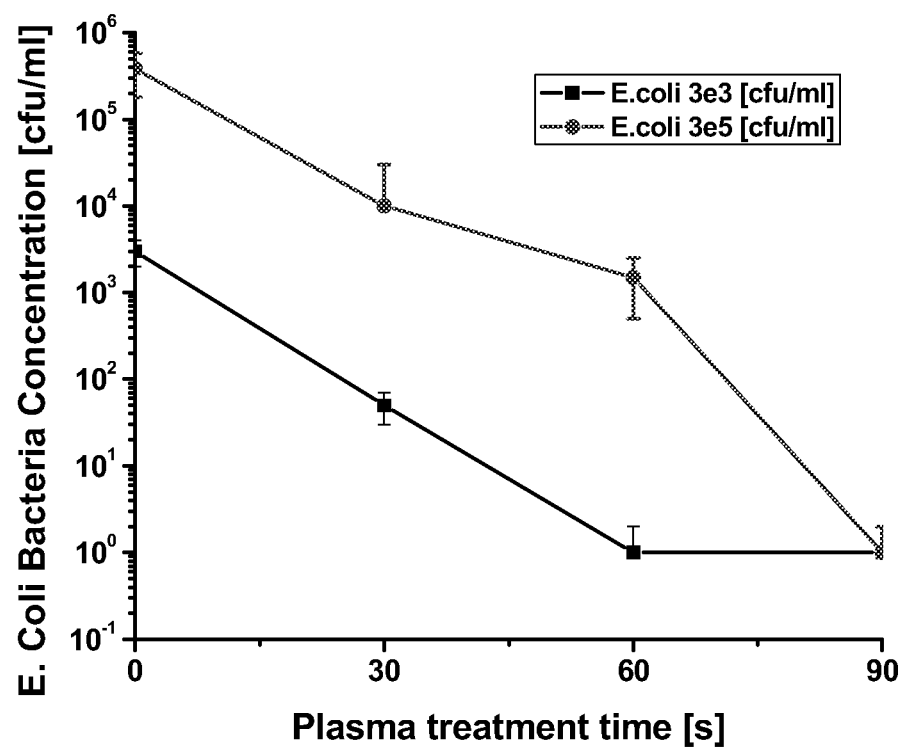
FIG. 22 shows the results of *E. coli* inactivation by plasma treated water, showing that 60 sec treatment was sufficient to inactivate $2\times10^3$ CFU/mL *E. Coli*. Times of 30 s, 60 s, and 90 s correspond to plasma energies of 3.9, 7.8, and 11.9 J/cm², respectively

FIG. 22 shows changes in of *E. coli* concentration as a function of plasma treatment time for two different initial concentrations of $3\times10^5$ and $2\times10^3$ CFU/mL. For this experiment, 25 μl of *E. coli* was dried on a glass slide (to prevent an interference of organics that might have been present in *E. coli* medium) then mixed with plasma treated water, after 2 min (holding time) was plated and counted following 24 hour incubation. In both cases bacteria were fully inactivated by plasma treated water for treatment time of 90 sec (11.7 J/cm$^2$).

Experiments without Organic Materials Added—Series 2

Experimental Conditions—*E. coli* aliquots of 9-, 8-, 7-, and 6-Log 10 CFU/ml were prepared from fresh overnight cultures in trypticase soy broth (TSB) to generate killing curves. For biofilms, the overnight culture was diluted to 1:100 in TSB and allowed to established biofilms for 24 h/37° C. (detected by microplate/Safranin assay). Phosphate-buffered saline (PBS) was exposed to plasma for various time (amount of plasma energy) and the culture aliquot or biofilm bearing surface was then treated with it, and processed further for the demonstration of percent surviving cells. In another set, the 1:100 diluted overnight-cultures was mixed with plasma-treated PBS and incubated as above. Standard colony count assay, Safranin assay, XTT assay and Live/Dead BacLight bacterial viability kit were used for this purpose. The Plasma energy was generated corresponding to energies ($J/cm^2$) as a function of time of 0 (0 sec), 1.95 (15 sec), 3.9 (30 sec), 7.8 (60 sec), and 11.7 (90 sec), 15.6 (120 sec), 23.4 (180 sec), 39 (300 sec).

Results—A plasma (energy) dose-dependent and bacterial cell density-dependent killing responses were observed in all three conditions of $E.\ coli$. To 30 second's plasma exposure (3.9 $J/cm^2$), planktonic forms resulted in about 60%, 89%, 97% and 100% killing of respectively 9, 8, 7, and 6 Log 10 cells. Biofilm-embedded $E.\ coli$ were 100% killed (treatment of biofilms) in 120 seconds, and were comparable to 70% ethanol treated biofilms (for 1 h). The exposure of plasma-treated PBS resulted in significant reduction ($p<0.05$) in biofilm formation (prevention of biofilms). The findings of colony assay, XTT and BacLight assay were comparable.

Experiments without Organic Materials Added—Series 3

Culture and Isolates of bacterial pathogens: $E.\ coli$, $S.\ aureus$ (also referred as methicillin-sensitive $S.\ aureus$, MSSA, occasionally), MRSA USA300 (BAA-1680) and MRSA USA400 (BAA-1683) strains were purchased from American type culture collection (ATCC, Manassas, Va.). Clinical isolates of MRSA (referred as MRSA95) was isolated from Hahnemann University Hospital's clinical laboratory from patients with skin and soft tissue infection, and identified by API and VITEK 2 automatic systems (BioMérieux, Inc., Durham, N.C.). All strains were maintained and used as overnight cultures in trypticase soy broth (TSB) for primary inoculations. Hydrogen peroxide or 70% Ethyl alcohol were used as known biocide agents, and either TSB alone or PBS alone as negative controls, as appropriate.

DBD-Plasma Generating Device, Parameters and Conditions: Experiments were done using a Floating-electrode DBD (FE-DBD) plasma generator, using a first electrode (which was a dielectric protected powered electrode) and a second electrode (the sample-carrying surface). The second electrode was not grounded and remains floating having potential to ignite discharge plasma when the powered (first) electrode approaches the surface to be treated. The diameter of plasma generating probe was 25 mm (sufficient for 15 mm diameter area under treatment). A low-frequency alternating current (120V) was generated and the desired output voltage and frequency (Hz) was obtained through a step transformer across the interface. A typical plasma power of 0.13 $W/cm^2$ was used for variable times of exposures in order to deposit desired amount of plasma energy ($J/cm^2$) to the sample to be treated. The micropulse mode has fair uniformity, and therefore uniform deposition of plasma energy is possible. In these experiments, 100 µl of phosphate-buffered saline (PBS, 150 mM sodium chloride and 150 mM sodium phosphate, pH 7.2 at 25° C.) was exposed to plasma being discharged, and 80 µl of treated PBS immediately applied (no delay time) to the surface or suspension of interest. The plasma energy ($J/cm^2$) levels which were used in the present research (otherwise stated) are as follows: 0 (0 seconds, s), 0.39 (3 s), 0.78 (6 s), 1.56 (12 s), 1.95 (15 s), 3.12 (24 s), 3.9 (30 s), 7.8 (60 s), 11.7 (90 s), 15.6 (120 s), and 19.5 (150 s), etc.

Plasma Bactericidal Activity and Planktonic Forms: The cultures of interest were inoculated as 10 µl primary cultures into 10 ml TSB medium and incubated at 37° C. for 24 h at 180 rpm and then appropriately diluted to obtain the desired number of cells (CFU/ml). Concurrently, the optical densities at 580 nm and colony count assays were performed in parallel to select the desired cell densities. In some of the early experiments, overnight cultures were used to prepare bacterial lawns on trypticase soy agar plates, and after plasma treatment or non-treatment, plates were incubated at 37° C. up to 48 h and observed periodically at 18 h, 24 h, and 48 h for zone of inhibition of growth. Samples of 25 µl of PBS was exposed to plasma and then immediately mixed with 25 µl of 2× cell suspension (to have final 1× cell suspension in PBS), held for 5 min before serial dilution for colony count. The plates were observed periodically as above, and colonies were counted to calculate total CFU/mL.

Bacterial Pathogens as Biofilms: Biofilms were developed for $E.\ coli$, $S.\ aureus$ (MSSA), MRSA-95, MRSA-USA300 and -USA400 in sterile 96 well plates (all Costar, Corning Inc., Corning, N.Y.). An overnight culture was diluted to 1:100 with sterile TSB, and 200 µl of suspension was applied to the 96-well plates, in triplicates to incubate for 24 h at 37° C. without shaking. The next day, fluid from the biofilm containing 96-well plates was gently aspirated, and washed three times with PBS, and either left untreated or treated with the plasma-treated PBS, and then washed two times post-treatment with PBS before treatment and then used for appropriate staining or detection of metabolic activity.

Safranin Assay: Biofilms developed in a 96-well plate were washed as above, and dried briefly by holding at 37° C. (20 min) to stain by the known Safranin microtiter plate method. The biofilms were stained with 200 µl of 0.1% aqueous solution of Safranin for 15 min. The excess stain was removed by washing three times with PBS. After addition of 70% ethanol the biofilm-containing wells were held at room temperature for 15 min. The plate was read in microtiter plate reader (Synergy, BioTek, Winooski, Vt.) after brief shaking (3 sec) at 550 nm. The well containing TSB alone plus Safranin was used as negative control to normalized readings. This Safranin assay is used for semi-quantification of biofilms, and is often the test used for detection of biofilms in clinical isolates.

Other Assays—The LIVE/DEAD BacLight Bacterial Viability assay kit is routinely used for detection of efficacy of bactericidal agents, and quantification of biofilms, and was used as recommended by the supplier (Molecular Probes, Invitrogen, CA).

For each XTT assay, fresh XTT reagent solutions were prepared as described earlier. From the aliquots, 0.5 mg XTT (Molecular Probe) and 1 uM Menadione (Sigma Chemical Co.) working solution was made up in 1×PBS. After appropriate treatment or no treatment, the microtubes containing samples of planktonic form of pathogen were spun at 8000 rpm/6 min, and supernatant discarded. The cells were resuspended in 200 µl of XTT reagent, mixed thoroughly, and tubes incubated at 37° C./2 h. After centrifugation, the supernatant (100 µl) containing orange colored XTT metabolic product was measured by reading absorption at 492 nm using a microtiter plate reader (Synergy Mx, BioTek). The readings were normalized and percent surviving cells were calculated against untreated samples. Similarly, the XTT assay for biofilms was carried out in the 96 well plates (200 µl for each well) and no spinning was involved.

Statistical Analysis of Data—The data from the experiments were analyzed using Prism software 4.03 for Windows (GraphPad, San Diego, Calif.), and standard deviations calculated from minimum three sets of experiments.

All the experiments were repeated in triplicate. The p-value was derived using pair comparisons between two bacterial groups using Student t-test and one way ANOVA for multiple comparisons wherever applicable (* indicates p value as a statistically significant ($p<0.05$)).

Results—Free living planktonic forms of E. coli, S. aureus and MRSA, exposed to DBD plasma-treated phosphate buffered saline (PBS) were rapidly inactivated under clinically useful scenarios. About $10^7$ bacterial cells were completely (100%) killed whereas $10^8$ and $10^9$ were reduced by about 90 to 95% and 40 to 45% respectively, in less than 60 seconds (7.8 $J/cm^2$) and completely disinfected in ≤120 seconds. In established biofilms, the susceptibility of MRSA USA400 was comparable to USA300, but less susceptible than MRSA95 (clinical isolate), S. aureus, and E. coli ($p<0.05$) to FE-DBD-plasma, and plasma was able to kill MRSA more than 60% within 15 seconds (1.95 $J/cm^2$). The killing responses were plasma-exposure time- and cell density-dependent. The plasma was able disinfect surfaces in a less than 120 seconds.

Figure 23:
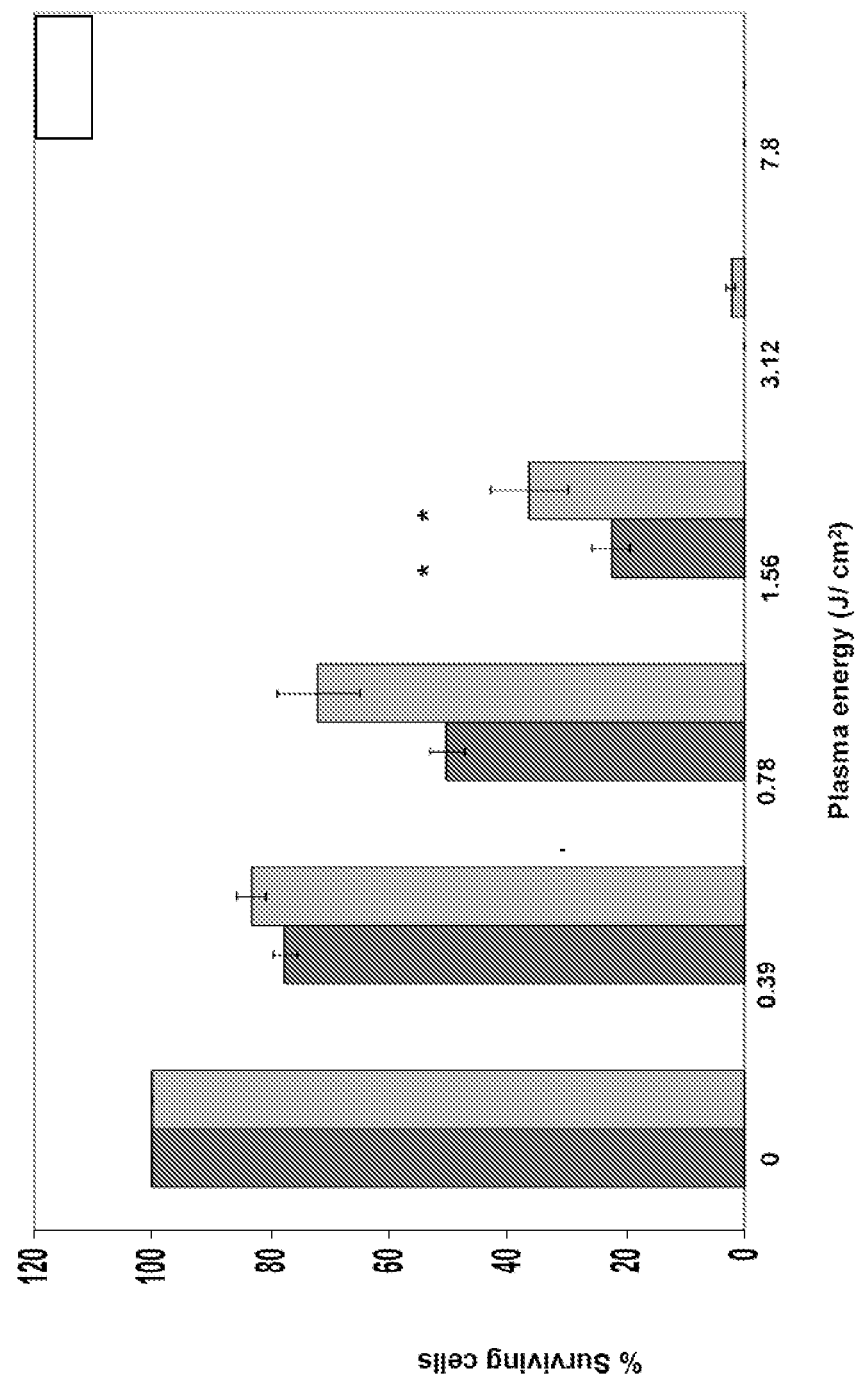
FIG. 23 shows the results of colony assays demonstrating a rapid inactivation of *E. coli* and *S. aureus* (at $10^7$ CFU/ml), by application of plasma-treated PBS (see Experiments Without Organic Materials Added—Series 3, below). The killing effect was plasma-exposure time dependent. The left bar within each plasma energy set indicates *E. coli*; the right bar indicates *S. aureus*, Bar, standard deviation; *, indicates statistically significant (p<0.05) inactivation as compare to the corresponding plasma non-treated cells

Dose-Dependent Responses of Planktonic Cultures and Surface Contaminants to Non-Thermal Plasma—The efficacy of plasma applications on representative bacteria (one each from gram-positive and gram-negative groups) were quantified using colony count assay methods described above. The findings of the colony count assay were highly reproducible, when carried in three to five sets, each in triplicate. As shown in FIG. 23, E. coli was significantly more susceptible as compared to S. aureus (which took little more plasma energy for comparable inactivation ($p<0.05$). Sterilization of both the organisms (at ~$10^7$ CFU/ml) was observed with PBS treated with 7.8 $J/cm^2$ plasma.

Figure 24:
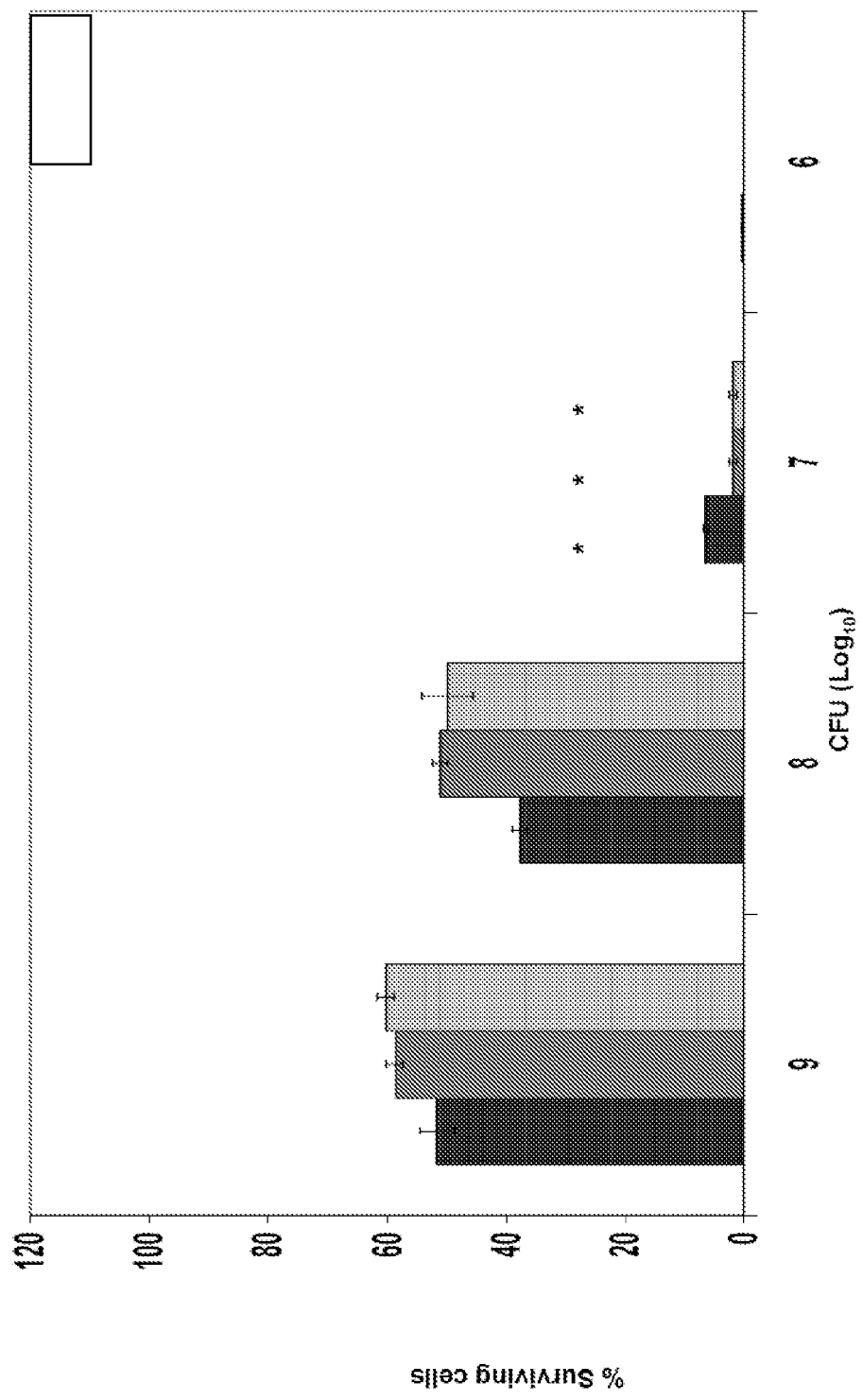
FIG. 24 shows the results of XTT assays demonstrating bacterial biomass-dependent responses towards applications of plasma-treated PBS (see Experiments Without Organic Materials Added—Series 3, below). The planktonic cultures ($10^6$ to $10^9$ CFU/ml) were exposed to 3.9 J/cm² (30 sec) of plasma energy. Bar, standard deviation; *, P<0.05 for given cell concentration as compare to plasma untreated cells; first bar from left within each CFU represents data for *E. coli*; second for *S. aureus*; and third for MRSA95

Time to Plasma-Mediated Sterilization is Proportional to Bacterial Load: The Cell-Density-Dependent Responses—A series of experiments were conducted using $10^9$, $10^8$, $10^7$, and $10^6$ CFU/ml to evaluate plasma's antibacterial efficacy. The inactivation process took a longer time for all the organisms, viz. E. coli, S. aureus, and MRSA95 at higher loads ($10^9$ CFU/ml) versus sterilization at $10^6$ CFU/ml when exposed to PBS treated with for 30 sec to either direct or indirect plasma. FIG. 24 indicates that plasma can be safely applied to achieve 100% disinfection of these organisms ($10^6$ CFU/ml), including multidrug resistant MRSA isolates in less than 30 sec (3.9 $J/cm^2$).

Figure 25:
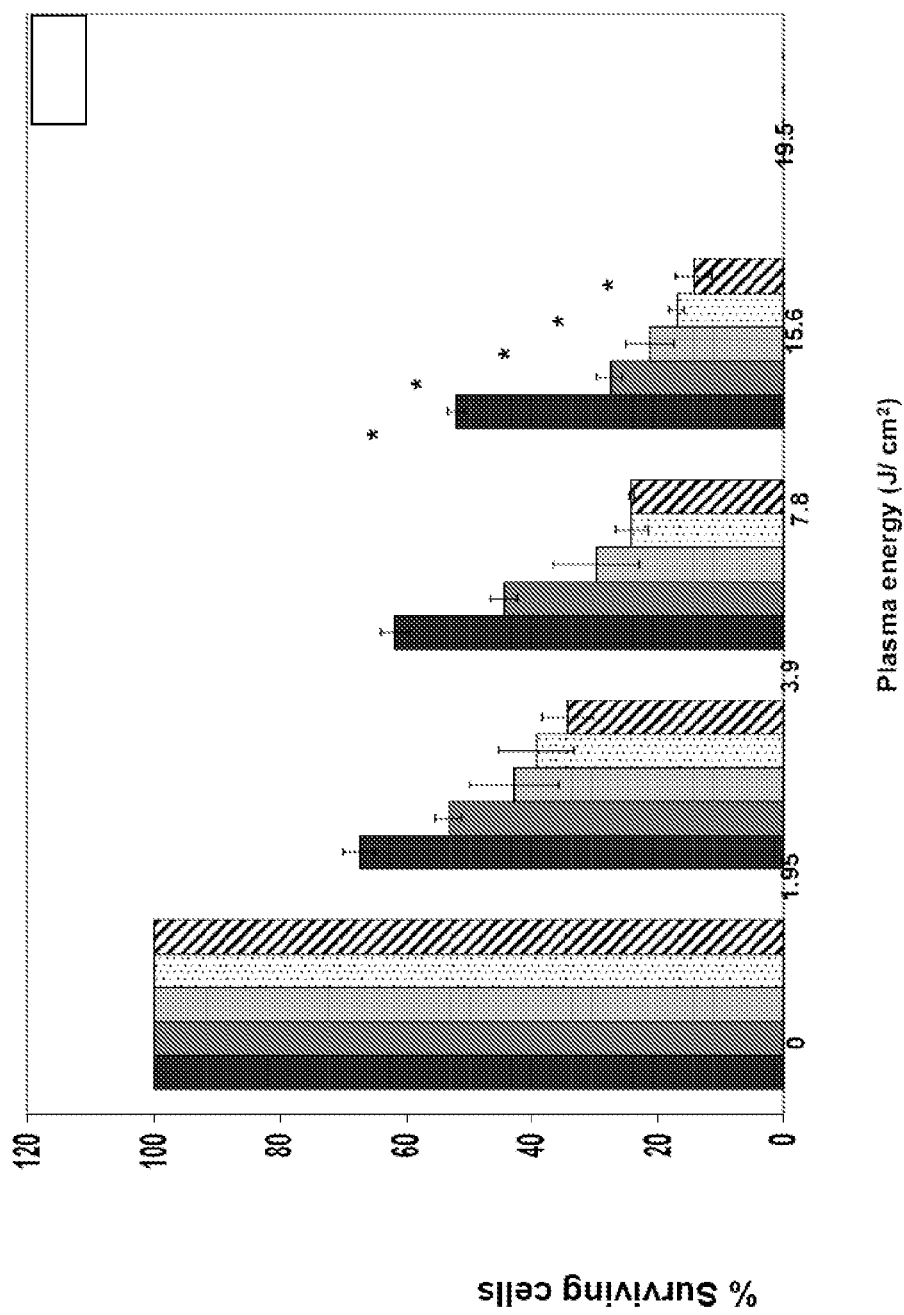
FIG. 25 shows the results of XTT assays showing a rapid inactivation of MRSA-USA300 and -USA400 when embedded in biofilms, upon applications of plasma-treated PBS (see Experiments Without Organic Materials Added—Series 3, below). All biofilm-embedded pathogens were inactivated in less than 150 seconds (required 19.5 J/cm² plasma energy). Bar, standard deviation; *, significant inactivation (p value <0.05) as compared to plasma non-treated bacteria or biofilms; first bar from left within each plasma energy field represents data for *E. coli*; second for *S. aureus*; third for MRSA95; fourth for USA300; and rightmost bar for USA400.
Figure 26A:
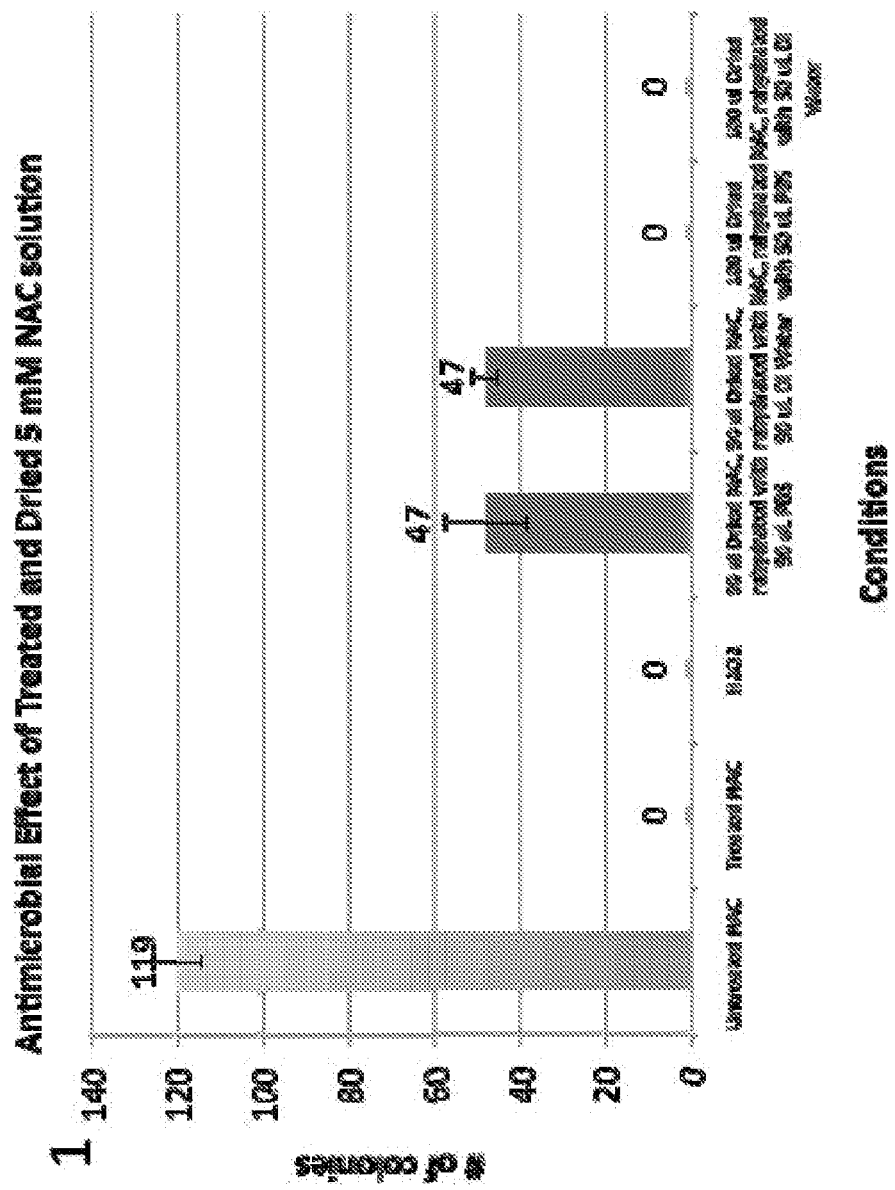
FIGS. 26A-D show the results of experiments aimed at determining the efficacy of plasma treating powders or solutions resulting in powders, as described below in section titled Preparing and Reconstituting Dry Powder Disinfectants.
Figure 26B:
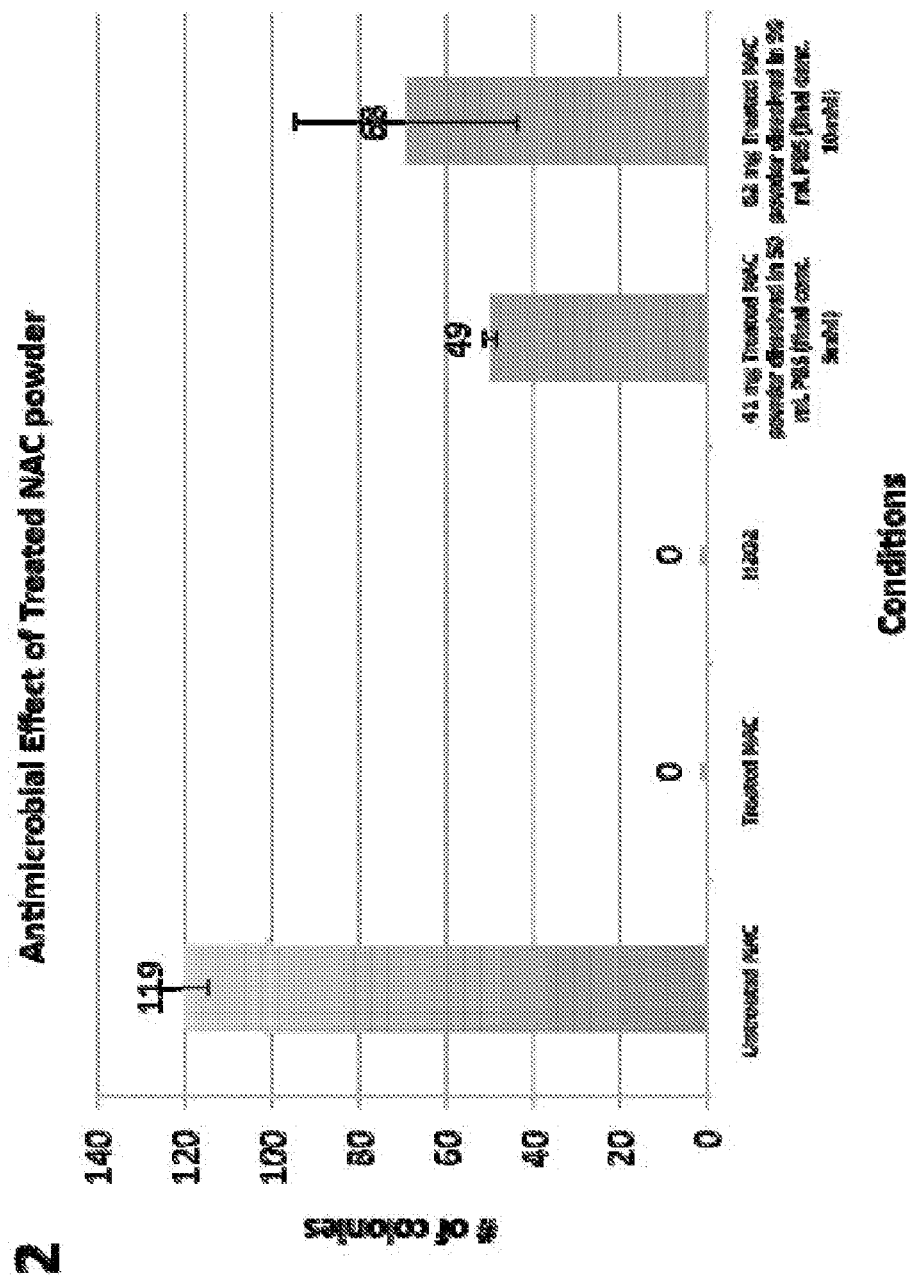
Figure 26C:
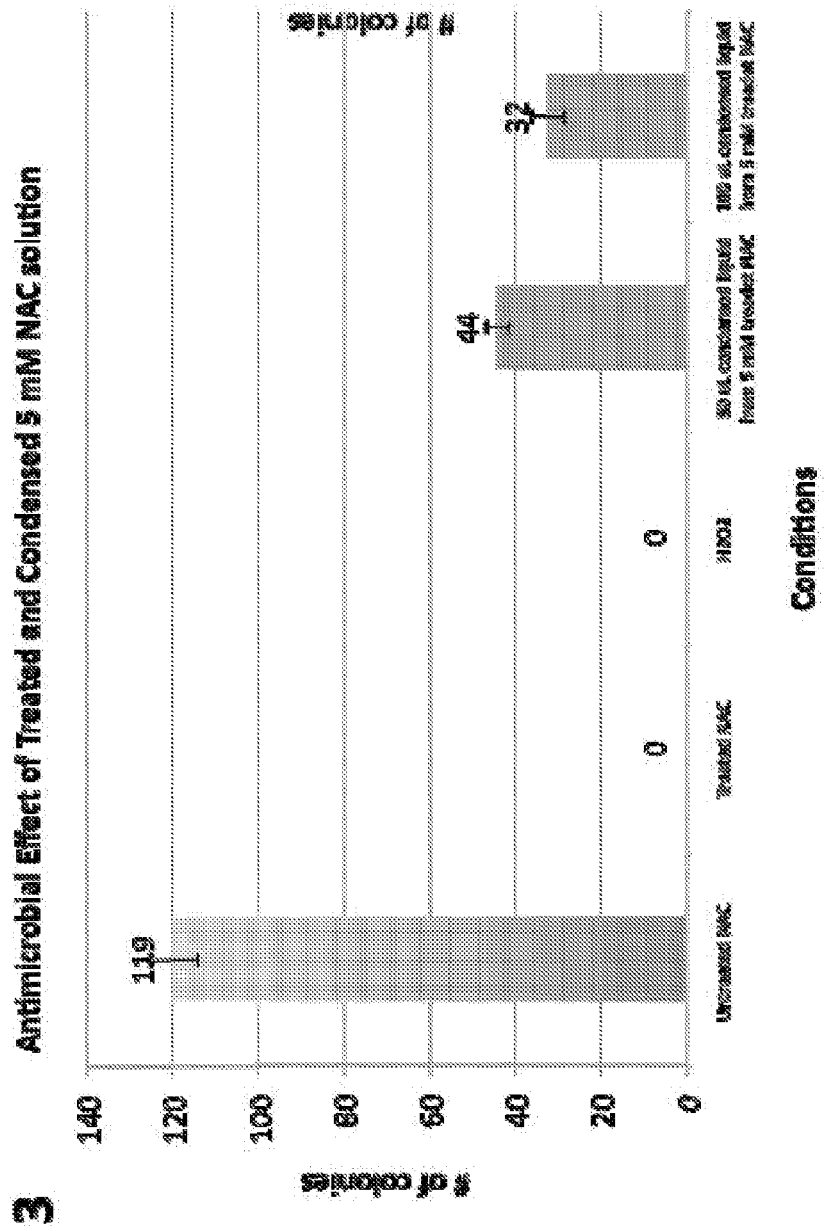
Figure 26D:
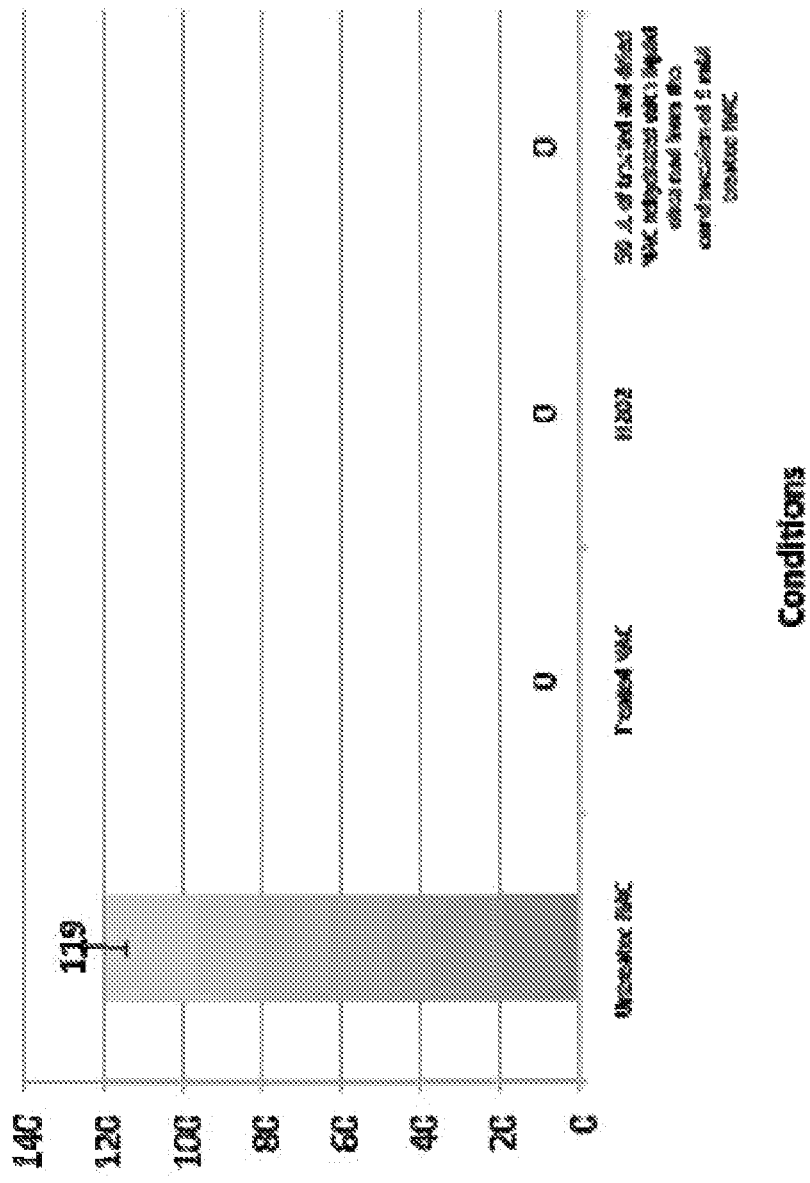

Plasma Potential of Sterilization of MRSA-USA300 and -USA400, in Both Planktonic & Embedded Biofilms Forms: Tests were also conducted using a multidrug resistant clinical MRSA isolate (MRSA95), and the most widely reported virulent biofilm-producing strains, the USA300 and USA400 for their comparative responses in the midst of biofilms. FIG. 25 demonstrates the percent survival for cells of all three MRSA strains tested in this study during plasma exposure. For comparison biofilms embedded E. coli and S. aureus (MSSA) strains were included in these tests. Given that the XTT assay is a gold standard to demonstrate viable cells, the XTT assay findings from FIG. 25 show that E. coli in biofilm form offers more resistance to plasma inactivation than S. aureus and USA 400 and USA 300 at various plasma energy levels. MRSA USA400 was slightly more resistant than MRSA USA300 in biofilm forms, when plasma was applied directly, but nevertheless the methodology sterilized all biofilm form of all the pathogens (all $p<0.05$) in less than 120 sec (15.6 $J/cm^2$). These tests also showed that the biofilms which are resistant to many of the powerful biocides were totally disinfected in a short time (<120 sec/<15.6 $J/cm^2$).

Experiments without Organic Materials Added—Series 4

An agar place of bacterial (containing colonies of $10^5$ E. coli) was placed on top of a grounded metal plate. A needled syringe containing 98% ethanol and having a drip rate of approximately 0.5 mL/min) was configured so that the needle was positioned 5" above the surface of the agar plate. A 10 kV positive polarity DC corona charge was attached to the needle, which generated an electric field between the tip of the needle and the grounded plate, the resulting corona discharge causing the dropping ethanol to aerosolize into a mist and be attracted to the surface of the agar plate. In separate duplicate experiments, treatment times of 5 sec, 15 sec, and 30 sec resulted in the complete disinfection of the *E. Coli*. In control experiments (i.e., no treatment), the bacteria showed no evidence of disinfection. In experiments wherein the alcohol was dispersed for 15 sec, but where no corona discharge was applied, some spotty effects were observed, but the sterilization was quantitatively less and less uniform than when the plasma was applied.

Preparing and Reconstituting Dry Powder Disinfectants

A series of experiments were conducted to determine the efficacy of powders obtained from plasma-treatment (either as solutions or powders) and compositions prepared from reconstituting the same. In these experiments, NAC was used as the disinfecting agent. FIG. 26A shows the results of a series of experiments in which NAC was partially dissolved in water to provide a dispersion of solid NAC in 5 mM NAC solution. The mixture was treated with plasma, the solid and liquid phases were separated, and the water was removed at room temperature from the liquid phase to provide a powder. The two solids were then separately rehydrated with PBS and deionized water. Equal portions (50 μL) of *E. coli* bacteria suspension and the rehydrated NAC were mixed together. FIG. 26B shows the results of testing when NAC powder was exposed to plasma treatment, rehydrated and tested. The test conditions used to generate FIGS. 26C &D were similar to those used to generate FIG. 26A, except that the solutions were heated after plasma treatment.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment but rather should be construed in breadth and scope in accordance with the appended claims.

As those skilled in the art will appreciate, numerous modifications and variations of the present invention are possible in light of these teachings, and all such are contemplated hereby. For the sake of brevity, each and every combination is not provided here, but the skilled artisan would appreciate that, in addition to the embodiments described herein, the present invention contemplates and claims those inventions resulting from the combination of each and every feature of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, in their entirety.

What is claimed:

1. A method comprising:
contacting an aqueous composition, the aqueous composition being an aqueous gel or water containing an organic material comprising an amino acid, with a plasma to form a disinfection composition, wherein the plasma is a dielectric barrier discharge, a corona or pulsed corona discharge, arc, spark, gliding arc, radio frequency discharge, or microwave discharge plasma.

2. The method of claim 1, wherein the aqueous composition is water, and the water is in the form of an aerosol or mist.

3. The method of claim 1, wherein the aqueous composition is water, and the water contains a saline or phosphate buffer composition, or a combination thereof.

4. The method of claim 1, wherein the aqueous composition is an aqueous gel, and the aqueous gel is an alginate gel.

5. The method of claim 1, wherein the aqueous composition is water, and the organic material comprises N-Acetyl Cysteine.

6. The method of claim 1, further comprising removing at least part of the water from the disinfection composition to form a dehydrated disinfection composition.

7. The method of claim 6, further comprising reconstituting the dehydrated disinfection composition to form a reconstituted disinfection composition.

8. The method of claim 7, further comprising the step of contacting the disinfection composition with a new surface, said surface being at least partially disinfected upon contact with the reconstituted disinfection composition.

9. The method of claim 1, further comprising the step of contacting the disinfection composition with a surface, said surface being at least partially disinfected upon contact with the disinfection composition.

10. The method of claim 9, wherein the surface comprises metal, plastic, glass, ceramic, a composite thereof, or a living tissue.

11. The method of claim 9, wherein the surface is contacted with the disinfection composition remote from the plasma.

12. The method of claim 9, wherein a period of time elapses between forming the disinfection composition and contacting the disinfection composition with the surface.

13. A disinfection composition prepared by the method of claim 1, prepared by contacting the aqueous gel or water containing an organic material comprising an amino acid with a plasma, wherein the plasma is a dielectric barrier discharge, a corona or pulsed corona discharge, arc, spark, gliding arc, radio frequency discharge, or microwave discharge plasma, wherein the disinfection composition is capable of at least partially disinfecting a surface.

14. A composition prepared by the method of claim 6.

15. The composition of claim 14, wherein the dehydrated disinfection composition is a powder.

16. A composition wherein the composition of claim 14 is reconstituted to form a liquid, aerosol, or both.

17. A product containing the disinfection composition claim 13, wherein the disinfection composition is provided on a woven or non-woven fabric.

* * * * *